United States Patent
Hanke et al.

(10) Patent No.: US 7,993,651 B2
(45) Date of Patent: Aug. 9, 2011

(54) CHIMERIC HUMAN IMMUNODEFICIENCY VIRUS (HIV) IMMUNOGENS COMPRISING GAG P24-P17 FUSED TO MULTIPLE CYTOTOXIC T LYMPHOCYTE (CTL) EPITOPES

(75) Inventors: Tomas Hanke, Oxford (GB); Andrew McMichael, Oxford (GB)

(73) Assignees: Medical Research Council, London (GB); International AIDS Vaccine Initiative, New York, NY (US); University of Nairobi, Nairobi (KE)

( * ) Notice: Subject to any disclaimer, the term of this patent is extended or adjusted under 35 U.S.C. 154(b) by 1740 days.

(21) Appl. No.: 10/168,843

(22) PCT Filed: Dec. 22, 2000

(86) PCT No.: PCT/GB00/04984
§ 371 (c)(1),
(2), (4) Date: Sep. 24, 2002

(87) PCT Pub. No.: WO01/47955
PCT Pub. Date: Jul. 5, 2001

(65) Prior Publication Data
US 2003/0108562 A1 Jun. 12, 2003

(30) Foreign Application Priority Data
Dec. 23, 1999 (GB) .................................. 9930294.5
Oct. 14, 2000 (GB) .................................. 0025234.6

(51) Int. Cl.
*A61K 39/21* (2006.01)
(52) U.S. Cl. .................................. 424/188.1; 424/208.1

(58) Field of Classification Search ........................ None
See application file for complete search history.

(56) References Cited

U.S. PATENT DOCUMENTS

| 4,629,783 A | 12/1986 | Cosand |
| 4,784,941 A | 11/1988 | Watanabe et al. |
| 4,808,536 A | 2/1989 | Chang et al. |

(Continued)

FOREIGN PATENT DOCUMENTS
EP 1 088 889 4/2001
(Continued)

OTHER PUBLICATIONS

Hanke, T., et al., 1998, "Immunogenicities of intravenous and intramuscular administrations of modified vaccinia virus Ankara-based multi-CTL epitope vaccine for human immunodeficiency virus type 1 in mice", J. Gen. Virol. 79(1):83-90.*

(Continued)

*Primary Examiner* — Jeffrey Parkin
(74) *Attorney, Agent, or Firm* — Vedder Price P.C.; Thomas J. Kowalski; Deborah L. Lu

(57) ABSTRACT

Disclosed is an immunogen in sterile form suitable for administration to a human subject, the immunogen comprising: at least a portion of the gag protein of HIV, said gag protein being from an HIV clade or having a consensus sequence for one or more HIV clades, and comprising at least parts of p17 and p24; and a synthetic polypeptide comprising a plurality of amino acid sequences, each sequence comprising a human CTL epitope of an HIV protein, and wherein a plurality of HIV proteins are represented in the synthetic polypeptide, said CTL epitopes being selected to stimulate an immune response to one or more HIV clades of interest.

15 Claims, 11 Drawing Sheets

```
  1 MPIVQNAQGQ MHQALSPRTL NAWVKVIEEK AFSPEVIPMF SALSEGATPQ  50
 51 DLNMMLNIVG GHQAAMQMLK DTINEEAAEW DRLHPVHAGP IPPGQMREPR 100
101 GSDIAGTTST LQEQIGWMTS NPPIPVGDIY KRWIILGLNK IVRMYSPVSI 150
151 LDIRQGPKEP PRDYVDRFFK TLRAEQATQE VKNWMTETLL VQNANPDCKS 200
201 ILRALGPGAT LEEMMTACQG VGGPGHKARV LGTGARASVL SGGKKLDAWEK 250
251 IRLRPGGKKK YRLKHLVWAS RELERFALNP SLLETAEGCQ QIMEQLQSAL 300
301 KTSEELKSLF NTVATLYCVH QRIDVKDTKE ALDKIEEIQN KSKQKTQQAA 350
351 ADTQSSSKVS QNYALKHRAY ELEFPPIPVG EIYKRWIIFR DYVDRFYKTL 400
401 RAIFQSSMTK ITLWQRPLVE RYLKDQQLLT VVYGVPVWKR PQVPLRPMTY 450
451 KAVDLSHFLK EKGGLILKEP VHGVYHPDIV IYQYMDDLTP GPGVRYPLAC 500
501 TPYDINQMLR GPGRAFVTIP NPLLGLD                         527
```

U.S. PATENT DOCUMENTS

| | | | |
|---|---|---|---|
| 4,822,606 | A | 4/1989 | Snyderman et al. |
| 5,134,227 | A | 7/1992 | Chang et al. |
| 5,175,097 | A | 12/1992 | Watanabe et al. |
| 5,175,098 | A | 12/1992 | Watanabe et al. |
| 5,210,181 | A | 5/1993 | Butman et al. |
| 5,328,835 | A | 7/1994 | Watanabe et al. |
| 5,459,238 | A | 10/1995 | McMichael et al. |
| 5,480,967 | A | 1/1996 | McMichael et al. |
| 5,576,421 | A * | 11/1996 | Saito et al. ............... 530/350 |
| 5,639,854 | A | 6/1997 | Sia et al. |
| 5,700,635 | A | 12/1997 | McMichael et al. |
| 5,759,769 | A | 6/1998 | Sia et al. |
| 5,759,770 | A | 6/1998 | Guertler et al. |
| 5,817,318 | A | 10/1998 | Sia et al. |
| 5,817,754 | A | 10/1998 | Sia et al. |
| 5,861,243 | A | 1/1999 | Dietrich et al. |
| 5,993,819 | A | 11/1999 | Haynes et al. |
| 6,111,068 | A | 8/2000 | Zimmerman et al. |
| 6,271,354 | B1 | 8/2001 | Srinivisan et al. |
| 6,395,891 | B1 | 5/2002 | Karn et al. |

FOREIGN PATENT DOCUMENTS

| | | |
|---|---|---|
| WO | WO 91/04051 | 4/1991 |
| WO | WO 98/06429 | 2/1998 |
| WO | WO 98/56919 | 12/1998 |
| WO | WO 00/15819 | 3/2000 |
| WO | WO 00/29008 | 5/2000 |
| WO | WO 00/39304 | 7/2000 |

OTHER PUBLICATIONS

Korber, B., et al., eds., 1999, HIV Molecular Immunology Database, Theoretical Biology and Biophysics Group, Los Alamos National Laboratory, Los Alamos, NM, I-A-19-I-A-45, I-A-50-I-A-74, I-A-82-I-A-116, and I-A-121-I-A-138.*

Kang, C. Y., et al., 1999, Development of HIV/AIDS Vaccine Using Chimeric Gag-Env Virus-Like Particles, Biol. Chem. 380:353-364.*

Hanke, T., et al., 1998, DNA Multi-CTL Epitope Vaccines for HIV and Plasmodium falciparum: Immunogenicity in Mice, Vaccine 16(4):426-435.*

Wagner, R., et al., 1992, Studies on Processing, Particle Formation, and Immunogenicity of the HIV-1 gag Gene Product: A Possible Component of a HIV Vaccine, Arch. Virol. 127:117-137.*

Frankel, F. R., 1995, Induction of Cell-Mediated Immune Responses to Human Immunodeficiency Virus Type 1 Gag Protein by Using Listeria monocytogenes as a Live Vaccine Vector, J. Immunol. 155:4775-4782.*

Bebbington, C. R. Expression of Antibody Genes in Nonlymphoid Mammalian Cells. Methods:Compan. Meth. Enzym. 2:136-145 (1991).

Berman, P. W. et al. Protection of chimpanzees from infection by HIV-1 after vaccination with the recombinant glycoprotein gp120 but not gp160. Nature 345:622-625 (1990).

Cao, H. et al. Cytotoxic T-lymphocyte cross-reactivity among different human immunodeficiency virus type 1 clades: Implications for vaccine development. J. Virol. 71:8615-8623 (1997).

Dorrell, L. et al. Distinct Recognition of Non-Clade B Human Immunodeficiency Virus Type 1 Epitopes by Cytotoxic T Lymphocytes Generated from Donors Infected in Africa. J. Virol. 73:1708-1714 (1999).

Fultz, P. N. et al. Vaccine Protection of Chimpanzees Against Challenge With HIV-1-Infected Peripheral Blood Mononuclear Cells. Science 256:16871690 (1992).

Gold, David. Cent Gardes Meeting: Researchers Increasingly Optimistic About Prospects for AIDS Vaccine. IAVI Report: (Nov. 1999) at www.iavi.org/reports/60/nov-dec-1999-1.html.

Goulder, Philip J. R. et al. Differential narrow focusing of immunodominant human immunodeficiency virus Gag-specific cytotoxic T-lymphocyte responses in infected African and Caucasoid adults and children. J. Virol. 74:5679-5690 (2000).

Hanke, T. et al. Immunogenicities of intravenous and intramuscular administration of modified vaccinia virus Ankara-based multi-CTL epitope vaccine for human immunodeficiency virus type 1 in mice. J. Gen. Virol. 79:83-90 (1998).

Hanke, T. et al. Construction of solid matrix-antibody-antigen complexes containing simian immunodeficiency virus p27 using tag-specific monoclonal and tag-linked antigen. J. Gen. Virol. 73:653-660 (1992).

Hanke, T. and McMichael, A. J. Design and construction of an experimental HIV-1 vaccine for a year-2000 clinical trial in Kenya. Nature Med. 6:951-955 (2000).

Hanke, T. et al. Enhancement of MHC class I-restricted peptide-specific T cell induction by a DNA prime/MVA boost vaccination regime. Vaccine 16:439-445 (1998).

Hanke, T. et al. DNA multi-CTL epitope vaccines for HIV and Plasmodium Falciparum: immunogenicity in mice. Vaccine 16:426-435 (1998).

Haynes, B.F. HIV vaccines: where we are and where we are going. Lancet 348:933-937 (1996).

Heilman, C. A. and Baltimore D. HIV vaccines-where are we going? Nature Med. Vacc. Suppl. 4:532-534 (1998).

Kwong, P. D. et al. Structure of an HIV gp120 envelope glycoprotein in complex with the CD$ receptor and a neutralizing human antibody. Nature 393:648-659 (1998).

McMichael, A. J. and Hanke, T. Is an HIV vaccine possible? Nature Med. 5:612-614 (1999).

Moore, John P. et al. Inter-and intraclade neutralization of human immunodeficiency virus type 1: Genetic clades do not correspond to neutralization gp120 antigenic serotypes. J. Virol. 70:427-444 (1996).

Rowland-Jones, S. L. et al. Cytotoxic T Cell Responses to Multiple Conserved HIV Epitopes in HIV-Resistant Prostitutes in Nairobi. J. Clin. Invest. 102:1758-1765 (1998).

Schneider J. et al. Enhanced immunogenicity for CD8+ T cell induction and complete protective efficacy of Malaria DNA vaccination by boosting with modified vaccinia virus Ankara. Nature Med. 4:397-402 (1998).

Sidney, J. et al. Practical, biochemical and evolutionary implications of the discovery of HLA class supermotifs. Immunol. Today 17:261-266 (1996).

Trkola, A. et al. Neutralization Sensitivity of Human Immunodeficiency Virus Type 1 Primary Isolates to Antibodies and CD4-Based Reagents Is Independent of Coreceptor Usage. J. Virol. 72:1876-1885 (1998).

Thomson S. A. et al. Recombinant polyepitope vaccines for the delivery of multiple CD8 cytotoxic T cell epitopes. J. Immunology. 157:822-826 (1996).

Whittle, N. et al. Expression in COS cells of a mouse-human chimaeric B72.3 antibody. Protein Engineering 1:499-505 (1987).

Williams S. G. et al. Repressor titration: a novel system for selection and stable maintenance of recombinant plasmids. Nucleic Acids Res. 26:2120-2124 (1998).

Woodberry, T. et al. Immunogenicity of a human immunodeficiency virus (HIV) polytope vaccine containing multiple HLA A2 HIV CD8+ cytotoxic T-cell epitopes. J. Virol. 73:5320-5325 (1999).

Wyatt, R. et al. The antigenic structure of the HIV gp 120 envelope glycoprotein. Nature 393:705-711 (1998).

Nucleotide and Protein databases, EBI, UK GAG Polyprotein, Accession No. 036574 (1998) XP002170220.

Nucleotide and Protein databases, EBI,UK Polyprotein, Accession No. 089962 (1998) XP002170221.

C. Yong Kang et al., "Development of HIV/AIDS Vaccine Using Chimeric gag-env Virus-Like Particles", Biol, Chem., vol. 380, pp. 353-364, Mar. 1999.

R. Wagner et al., "Studies on Processing, Particle Formation, and Immunogenicity if the HIV-1 gag gene product: a possible component of a HIV vaccine", Arch Virol (1992), vol. 127, No. 1 to 4, p. 117-137.

T. Hanke et al., "Immunogenicities of Intravenous and Intramuscular Administrations of modified vaccinia virus Ankara-based multi-CTL epitope vaccine for human immunodeficiency virus type 1 mice", Journal of General Virology (1998), vol. 79, No. 1, p. 83-90.

Kalams, et al., Association Between Virus-Specific Cytotoxic T-Lymphocyte and Helper . . ., J. of Virology (1999) vol. 73, No. 8, p. 6715-6720.

Seamus J. Martin, et al., Immunization Of Human HIV-Seronegative Volunteers With Recombinant p. 17/p. 24: Ty Virus-Like. . . , AIDS (1993) vol. 7, p. 1315-1323.

* cited by examiner

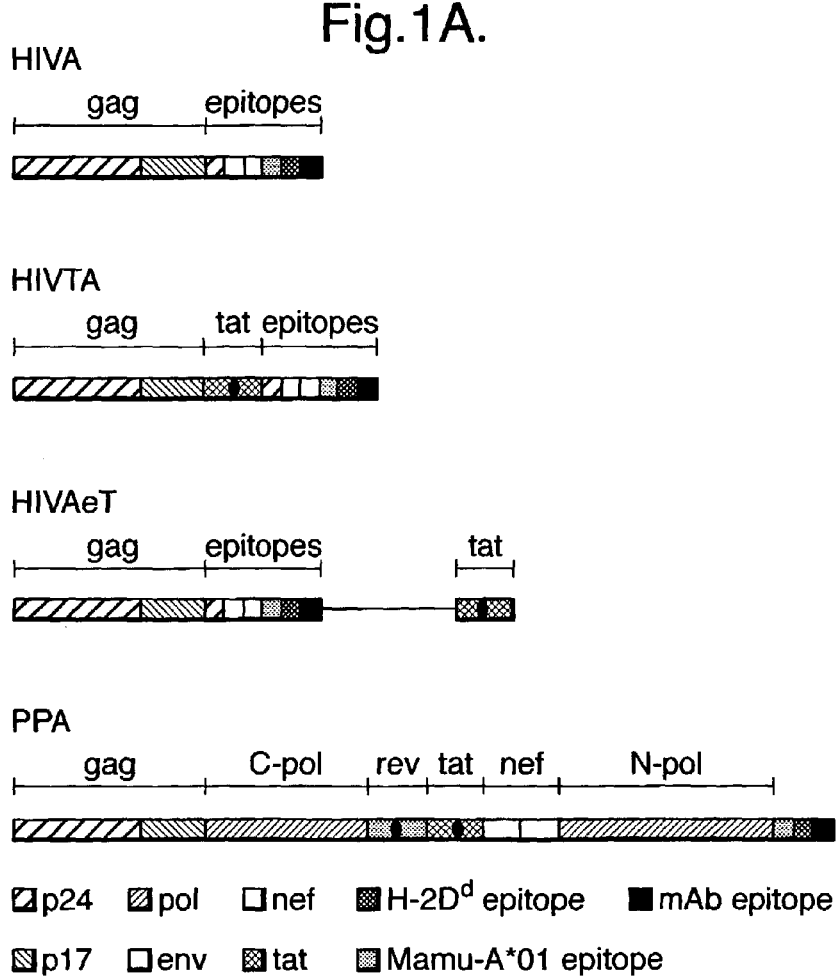

```
  1 MPIVQNAQGQ MHQALSPRTL NAWVKVIEEK AFSPEVIPMF SALSEGATPQ  50
 51 DLNMMLNIVG GHQAAMQMLK DTINEEAAEW DRLHPVHAGP IPPGQMREPR 100
101 GSDIAGTTST LQEQIGWMTS NPPIPVGDIY KRWIILGLNK IVRMYSPVSI 150
151 LDIRQGPKEP FRDYVDRFFK TLRAEQATQE VKNWMTETLL VQNANPDCKS 200
201 ILRALGPGAT LEEMMTACQG VGGPGHKARV LGTGARASVL SGGKLDAWEK 250
251 IRLRPGGKKK YRLKHLVWAS RELERFALNP SLLETAEGCQ QIMEQLQSAL 300
301 KTSEELKSLF NTVATLYCVH QRIDVKDTKE ALDKIEEIQN KSKQKTQQAA 350
351 ADTQSSSKVS QNYALKHRAY ELEFPPIPVG EIYKRWIIFR DYVDRFYKTL 400
401 RAIFQSSMTK ITLWQRPLVE RYLKDQQLLT VYYGVPVWKR PQVPLRPMTY 450
451 KAVDLSHFLK EKGGLILKEP VHGVYHPDIV IYQYMDDLTP GPGVRYPLAC 500
501 TPYDINQMLR GPGRAFVTIP NPLLGLD                         527
```

Fig.2A.

HIVA DNA
AAGCTTCCCGCCGCCACCATGCCCATCGTGCAGAACGCCCAGGGCCAGATGCACCAGGCC
CTGTCCCCCGCACCCTGAACGCCTGGGTGAAGGTGATCGAGGAGAAGGCCTTCTCCCCC
GAGGTGATCCCCATGTTCTCCGCCCTGTCCGAGGGCGCCACCCCCCAGGACCTGAACATG
ATGCTGAACATCGTGGGCGGCCACCAGGCCGCCATGCAGATGCTGAAGGACACCATCAAC
GAGGAGGCCGCCGAGTGGGACGCCTGCACCCCGTGCACGCCGGCCCCATCCCCCCCGGC
CAGATGCGCGAGCCCCGCGGATCCGACATCGCCGGCACCACCTCCACCCTGCAGGAGCAG
ATCGGCTGGATGACCTCCAACCCCCCCATCCCCGTGGGCGACATCTACAAGCGCTGGATC
ATCCTGGGCCTGAACAAGATCGTACGCATGTACTCCCCCGTGTCCATCCTGGACATCCGC
CAGGGCCCCAAGGAGCCCTTCCGCGACTACGTGGACCGCTTCTTCAAGACCCTGCGCGCC
GAGCAGGCCACCCAGGAGGTGAAGAACTGGATGACCGAGACCCTGCTGGTGCAGAACGCC
AACCCCGACTGCAAGTCCATCCTGCGCGCCCTGGGCCCCGGCGCCACCCTGGAGGAGATG
ATGACCGCCTGCCAGGGCGTGGGCGGCCCCGGCCACAAGGCCCGCGTGCTGGGTACCGGC
GCCCGCGCCTCCGTGCTGTCCGGCGGCAAGCTGGACGCCTGGGAGAAGATCCGCCTGCGC
CCCGGCGGCAAGAAGAAGTACCGCCTGAAGCACCTGGTGTGGGCCTCCCGCGAGCTGGAG
CGCTTCGCCCTGAACCCCTCCCTGCTGGAGACCGCCGAGGGCTGCCAGCAGATCATGGAG
CAGCTGCAGTCCGCCCTGAAGACCTCCGAGGAGCTGAAGTCCCTGTTCAACACCGTGGCC
ACCCTGTACTGCGTGCACCAGCGCATCGACGTGAAGGACACCAAGGAGGCCCTGGACAAG
ATCGAGGAGATCCAGAACAAGTCCAAGCAGAAGACCCAGCAGGCCGCCGCCGACACCCAG
TCCTCCTCCAAGGTGTCCCAGAACTACGCCCTGAAGCACCGCGCCTACGAGCTGGAATTC
CCTCCAATTCCTGTCGGGGAGATTTATAAACGGTGGATCATTTTTAGGGATTATGTCGAT
AGGTTTTATAAAACGCTCAGGGCCATCTTCCAGTCCTCCATGACCAAGATCACCCTGTGG
CAGCGCCCCTGGTGGAGCGCTACCTGAAGGACCAGCAGCTGCTGACCGTGTACTACGGC
GTGCCCGTGTGGAAGCGCCCCAGGTGCCCCTGCGCCCCATGACCTACAAGGCCGTGGAC
CTGTCCCACTTCCTGAAGGAGAAGGGCGGCCTGATCCTGAAGGAGCCCGTGCACGGCGTG
TACCACCCCGACATCGTGATCTACCAGTACATGGACGACCTGACCCCCGGCCCCGGCGTG
CGCTACCCCCTGGCCTGCACCCCCTACGACATCAACCAGATGCTGCGCGGCCCCGGCCGC
GCCTTCGTGACCATCCCCAACCCCCTGCTGGGCCTGGACTGATCTAGA

Fig.6B.

HIVTA DNA
CCCGCCGCCACCATGCCCATCGTGCAGAACGCCCAGGGCCAGATGCACCAGGCCCTGTCC
CCCCGCACCCTGAACGCCTGGGTGAAGGTGATCGAGGAGAAGGCCTTCTCCCCCGAGGTG
ATCCCCATGTTCTCCGCCCTGTCCGAGGGCGCCACCCCCCAGGACCTGAACATGATGCTG
AACATCGTGGGCGGCCACCAGGCCGCCATGCAGATGCTGAAGGACACCATCAACGAGGAG
GCCGCCGAGTGGGACCGCCTGCACCCCGTGCACGCCGGCCCCATCCCCCCCGGCCAGATG
CGCGAGCCCCGCGGATCCGACATCGCCGGCACCACCTCCACCCTGCAGGAGCAGATCGGC
TGGATGACCTCCAACCCCCCCATCCCCGTGGGCGACATCTACAAGCGCTGGATCATCCTG
GGCCTGAACAAGATCGTGCGCATGTACTCCCCCGTGTCCATCCTGGACATCCGCCAGGGC
CCCAAGGAGCCCTTCCGCGACTACGTGGACCGCTTCTTCAAGACCCTGCGCGCCGAGCAG
GCCACCCAGGAGGTGAAGAACTGGATGACCGAGACCCTGCTGGTGCAGAACGCCAACCCC
GACTGCAAGTCCATCCTGCGCGCCCTGGGCCCCGGCGCCACCCTGGAGGAGATGATGACC
GCCTGCCAGGGCGTGGGCGGCCCCGGCCACAAGGCCCGCGTGCTGGGTACCGGCGCCCGC
GCCTCCGTGCTGTCCGGCGGCAAGCTGGACGCCTGGGAGAAGATCCGCCTGCGCCCCGGC
GGCAAGAAGAAGTACCGCCTGAAGCACCTGGTGTGGGCCTCCCGCGAGCTGGAGCGCTTC
GCCCTGAACCCCTCCCTGCTGGAGACCGCCGAGGGCTGCCAGCAGATCATGGAGCAGCTG
CAGTCCGCCCTGAAGACCTCCGAGGAGCTGAAGTCCCTGTTCAACACCGTGGCCACCCTG
TACTGCGTGCACCAGCGCATCGACGTGAAGGACACCAAGGAGGCCCTGGACAAGATCGAG
GAGATCCAGAACAAGTCCAAGCAGAAGACCCAGCAGGCCGCCGCCGACACCCAGTCCTCC
TCCAAGGTGTCCCAGAACTACGCCCTGAAGCACCGCGCCTACGAGCTGGAATTCATGGCC
ACAACCATGGACCCCGTGGACCCCAACCTGGAGCCCTGGAACCACCCCGGCTCCCAGCCC
ACCACCCCCGGCTCCAAGTGCTACTGCAAGGTGTGCTGCTACCACTGCCCCGTGTGCTTC
CTGAACAAGGGCCTGGGCATCTCCTACGGCCGCAAGAAGCGCCGCCAGCGCCGCGGCACC
CCCCAGTCCAACAAGGACCACCAGAACCCCATCCCCAAGCAGCCCATCCCCCAGACCCAG
GGCATCTCCACCGGtCCCAAGGAGTCCAAGAAGAAGGTGGAGTCCAAGACCGAGACCGAC
CCCGAGGAATTCCCTCCAATTCCTGTCGGGGAGATTTATAAACGGTGGATCATTTTTAGG
GATTATGTCGATAGGTTTTATAAAACGCTCAGGGCCATCTTCCAGTCCTCCATGACCAAG
ATCACCCTGTGGCAGCGCCCCCTGGTGGAGCGCTACCTGAAGGACCAGCAGCTGCTGACC
GTGTACTACGGCGTGCCCGTGTGGAAGCGCCCCCAGGTGCCCCTGCGCCCCATGACCTAC
AAGGCCGTGGACCTGTCCCACTTCCTGAAGGAGAAGGGCGGCCTGATCCTGAAGGAGCCC
GTGCACGGCGTGTACCACCCCGACATCGTGATCTACCAGTACATGGACGACCTGACCCCC
GGCCCCGGCGTGCGCTACCCCCTGGCCTGCACCCCCTACGACATCAACCAGATGCTGCGC
GGCCCCGGCCGCGCCTTCGTGACCATCCCCAACCCCCTGCTGGGCCTGGACTGA

Fig.6A.

HIVTA protein
MPIVQNAQGQMHQALSPRTLNAWVKVIEEKAFSPEVIPMFSALSEGATPQDLNM
MLNIVGGHQAAMQMLKDTINEEAAEWDRLHPVHAGPIPPGQMREPRGSDIAGT
TSTLQEQIGWMTSNPPIPVGDIYKRWIILGLNKIVRMYSPVSILDIRQGPKEPFRDY
VDRFFKTLRAEQATQEVKNWMTETLLVQNANPDCKSILRALGPGATLEEMMTA
CQGVGGPGHKARVLGTGARASVLSGGKLDAWEKIRLRPGGKKKYRLKHLVWA
SRELERFALNPSLLETAEGCQQIMEQLQSALKTSEELKSLFNTVATLYCVHQRIDV
KDTKEALDKIEEIQNKSKQKTQQAAADTQSSSKVSQNYALKHRAYELEFMATTM
DPVDPNLEPWNHPGSQPTTPGSKCYCKVCCYHCPVCFLNKGLGISYGRKKRQR
RGTPQSNKDHQNPIPKQPIPQTQGISTGPKESKKKVESKTETDPEEFPPIPVGEIYK
RWIIFRDYVDRFYKTLRAIFQSSMTKITLWQRPLVERYLKDQQLLTVYYGVPVW
KRPQVPLRPMTYKAVDLSHFLKEKGGLILKEPVHGVYHPDIVIYQYMDDLTPGP
GVRYPLACTPYDINQMLRGPGRAFVTIPNPLLGLD

Fig. 7B.

HIVAeT DNA
CCCGCCGCCACCATGCCCATCGTGCAGAACGCCCAGGGCCAGATGCACCAGGCCCTGTCC
CCCCGCACCCTGAACGCCTGGGTGAAGGTGATCGAGGAGAAGGCCTTCTCCCCCGAGGTG
ATCCCCATGTTCTCCGCCCTGTCCGAGGGCGCCACCCCCCAGGACCTGAACATGATGCTG
AACATCGTGGGCGGCCACCAGGCCGCCATGCAGATGCTGAAGGACACCATCAACGAGGAG
GCCGCCGAGTGGGACCGCCTGCACCCCGTGCACGCCGGCCCCATCCCCCCCGGCCAGATG
CGCGAGCCCCGCGGATCCGACATCGCCGGCACCACCTCCACCCTGCAGGAGCAGATCGGC
TGGATGACCTCCAACCCCCCATCCCCGTGGGCGACATCTACAAGCGCTGGATCATCCTG
GGCCTGAACAAGATCGTGCGCATGTACTCCCCGTGTCCATCCTGGACATCCGCCAGGGC
CCCAAGGAGCCCTTCCGCGACTACGTGGACCGCTTCTTCAAGACCCTGCGCGCCGAGCAG
GCCACCCAGGAGGTGAAGAACTGGATGACCGAGACCCTGCTGGTGCAGAACGCCAACCCC
GACTGCAAGTCCATCCTGCGCGCCCTGGGCCCCGGCGCCACCCTGGAGGAGATGATGACC
GCCTGCCAGGGCGTGGGCGGCCCCGGCCACAAGGCCCGCGTGCTGGGTACCGGCGCCCGC
GCCTCCGTGCTGTCCGGCGGCAAGCTGGACGCCTGGGAGAAGATCCGCCTGCGCCCCGGC
GGCAAGAAGAAGTACCGCCTGAAGCACCTGGTGTGGGCCTCCCGCGAGCTGGAGCGCTTC
GCCCTGAACCCCTCCCTGCTGGAGACCGCCGAGGGCTGCCAGCAGATCATGGAGCAGCTG
CAGTCCGCCCTGAAGACCTCCGAGGAGCTGAAGTCCCTGTTCAACACCGTGGCCACCCTG
TACTGCGTGCACCAGCGCATCGACGTGAAGGACACCAAGGAGGCCCTGGACAAGATCGAG
GAGATCCAGAACAAGTCCAAGCAGAAGACCCAGCAGGCCGCCGCCGACACCCAGTCCTCC
TCCAAGGTGTCCCAGAACTACGCCCTGAAGCACCGCGCCTACGAGCTGGAATTCCCTCCA
ATTCCTGTCGGGGAGATTTATAAACGGTGGATCATTTTTAGGGATTATGTCGATAGGTTT
TATAAAACGCTCAGGGCCATCTTCCAGTCCTCCATGACCAAGATCACCCTGTGGCAGCGC
CCCCTGGTGGAGCGCTACCTGAAGGACCAGCAGCTGCTGACCGTGTACTACGGCGTGCCC
GTGTGGAAGCGCCCCCAGGTGCCCCTGCGCCCCATGACCTACAAGGCCGTGGACCTGTCC
CACTTCCTGAAGGAGAAGGGCGGCCTGATCCTGAAGGAGCCCGTGCACGGCGTGTACCAC
CCCGACATCGTGATCTACCAGTACATGGACGACCTGACCCCCGGCCCCGGCGTGCGCTAC
CCCCTGGCCTGCACCCCCTACGACATCAACCAGATGCTGCGCGGCCCCGGCCGCGCCTTC
GTGACCATCCCCAACCCCCTGCTGGGCCTGGACTGAGCGGCCGCCCCTCTCCCTCCCCCC
CCCCTAACGTTACTGGCCGAAGCCGCTTGGAATAAGGCCGGTGTGCGTTTGTCTATATGT
TATTTTCCACCATATTGCCGTCTTTTGGCAATGTGAGGGCCCGGAAACCTGGCCCTGTCT
TCTTGACGAGCATTCCTAGGGGTCTTTCCCCTCTCGCCAAAGGAATGCAAGGTCTGTTGA
ATGTCGTGAAGGAAGCAGTTCCTCTGGAAGCTTCTTGAAGACAAACAACGTCTGTAGCGA
CCCTTTGCAGGCAGCGGAACCCCCCACCTGGCGACAGGTGCCTCTGCGGCCAAAAGCCAC
GTGTATAAGATACACCTGCAAAGGCGGCACAACCCCAGTGCCACGTTGTGAGTTGGATAG
TTGTGGAAAGAGTCAAATGGCTCTCCTCAAGCGTATTCAACAAGGGGCTGAAGGATGCCC
AGAAGGTACCCCATTGTATGGGATCTGATCTGGGGCCTCGGTGCACATGCTTTACATGTG
TTTAGTCGAGGTTAAAAAAACGTCTAGGCCCCCGAACCACGGGGACGTGGTTTTCCTTT
GAAAAACACGATGATAATATGGCCACAACCATGGACCCCGTGGACCCCAACCTGGAGCCC
TGGAACCACCCCGGCTCCCAGCCCACCACCCCCGGCTCCAAGTGCTACTGCAAGGTGTGC
TGCTACCACTGCCCCGTGTGCTTCCTGAACAAGGGCCTGGGCATCTCCTACGGCCGCAAG
AAGCGCCGCCAGCGCCGCGGCACCCCCCAGTCCAACAAGGACCACCAGAACCCCATCCCC
AAGCAGCCCATCCCCCAGACCCAGGGCATCTCCACCGGCCCCAAGGAGTCCAAGAAGAAG
GTGGAGTCCAAGACCGAGACCGACCCCGAGTAA

Fig. 7A.

HIVAeT protein – TAT (HIVA is the same as above)
MATTMDPVDPNLEPWNHPGSQPTTPGSKCYCKVCCYHCPVCFLNKGLGISYGR
KKRRQRRGTPQSNKDHQNPIPKQPIPQTQGISTGPKESKKKVESKTETDPE

Fig.8A.

PPA protein
MPIVQNAQGQMHQALSPRTLNAWVKVIEEKAFSPEVIPMFSALSEGATPQDLNM
MLNIVGGHQAAMQMLKDTINEEAAEWDRLHPVHAGPIPPGQMREPRGSDIAGT
TSTLQEQIGWMTSNPPIPVGDIYKRWIILGLNKIVRMYSPVSILDIRQGPKEPFRDY
VDRFFKTLRAEQATQEVKNWMTETLLVQNANPDCKSILRALGPGATLEEMMTA
CQGVGGPGHKARVLGTGARASVLSGGKLDAWEKIRLRPGGKKKYRLKHLVWA
SRELERFALNPSLLETAEGCQQIMEQLQSALKTSEELKSLFNTVATLYCVHQRIDV
KDTKEALDKIEEIQNKSKQKTQQAAADTQSSSKVSQNYALKHRAYELEFGIKVK
QLCKLLRGAKALTDIVTLTEEAELELAENREILKDPVHGVYYDPSKDLIAEIQKQ
GQDQWTYQIYQEPFKNLKTGKYARKRSAQTNDVKQLAEVVQKVVMESIVIWGK
TPKFRLPIQKETWETWWMDYWQATWIPEWEFVNTPPLVKLWYQLEKDPIAGAE
TFYVDGAANRETKLGKAGYVTDRGRQKVVSLTETTNQKTELHVIHLALQDSGSE
VNIVTDSQYALGIIQAQPDRSDPVDPNLEPWNHPGSQPTTPGSKCYCKVCCYHCP
VCFLNKGLGISYGRKKRRQRRGTPQSNKDHQNPIPKQPIPQTQGISTGPKESKKK
VESKTETDPEDAGRSGNSDEELLKAIRIIKILYQSNPYPKPKGSRQARKNRRRRWR
AGQRQIDSLSERILSTCLGRPAEPVPLQLPPLELDCSEDCGTSGTQQSQGAETGVG
RPQVSVESSAVLGSGTKEGTVRPQVPLRPMTYKAAFDLSFFLKEKGGLDGLIYSK
KRQEILDLWVYHTQGYFPDWQNYTPGPGIRYPLTFGWCFKLVPVDPDEVEEATG
GENNSLLHPICQHGMDDEEKETLRWKFDSSLALKHRARELHPESYKDCPQITLW
QRPLVTKIGGQKTRGGKWSKSSIVGWPEVRERIRQTPTAARERTRQAPTAAKVG
AVSQDLDKHGAVSSNVNHPSCAWLEAQEEEVGFPELLDTGADDTVLEDINLPG
KWKPKMIGGIGGLIKVKQYDQILIEICGKKAIGTVLVGPTPVNIIGRNMLTQIGCTL
NFPISPIETVPVKLKPGMDGPKVKQWPLTEEKIKALTEICADMEKEGKISKIGPEN
PYNTPIFAIKKKQSTKWRKLVDFRELNKRTQDFWEVQLGIPHPAGLKKKKSVTV
LDVGDAYFSVPLDESFRKYTAFTIPSTNNETPGVRYQYNVLPQGWKGSPIFQSSM
TKILEPFRSKNPDIVIYQYMDDLYVGSDLEIGQHRTKIEELRAHLLSWGFITPDKK
HQKEPPFLWMGYELHPDKWTVQPIELPEKDSWTVNDIQKLVGKLNWASQIYAC
TPYDINQMLRGPGRAFVTIPNPLLGLD

Fig. 8B.

PPA DNA
```
CCCGCCGCCACCATGCCCATCGTGCAGAACGCCCAGGGCCAGATGCACCAGGCCCTGTCC
CCCCGCACCCTGAACGCCTGGGTGAAGGTGATCGAGGAGAAGGCCTTCTCCCCCGAGGTG
ATCCCCATGTTCTCCGCCCTGTCCGAGGGCGCCACCCCCAGGACCTGAACATGATGCTG
AACATCGTGGGCGGCCACCAGGCCGCCATGCAGATGCTGAAGGACACCATCAACGAGGAG
GCCGCCGAGTGGGACCGCCTGCACCCCGTGCACGCCGGCCCCATCCCCCCCGGCCAGATG
CGCGAGCCCCGCGGATCCGACATCGCCGGCACCACCTCCACCCTGCAGGAGCAGATCGGC
TGGATGACCTCCAACCCCCCATCCCCGTGGGCGACATCTACAAGCGCTGGATCATCCTG
GGCCTGAACAAGATCGTGCGCATGTACTCCCCCGTGTCCATCCTGGACATCCGCCAGGGC
CCCAAGGAGCCCTTCCGCGACTACGTGGACCGCTTCTTCAAGACCCTGCGCGCCGAGCAG
GCCACCCAGGAGGTGAAGAACTGGATGACCGAGACCCTGCTGGTGCAGAACGCCAACCCC
GACTGCAAGTCCATCCTGCGCGCCCTGGGCCCCGGCGCCACCCTGGAGGAGATGATGACC
GCCTGCCAGGGCGTGGGCGGCCCCGGCCACAAGGCCCGCGTGCTGGGTACCGGCGCCCGC
GCCTCCGTGCTGTCCGGCGGCAAGCTGGACGCCTGGGAGAAGATCCGCCTGCGCCCCGGC
GGCAAGAAGAAGTACCGCCTGAAGCACCTGGTGTGGGCCTCCCGCGAGCTGGAGCGCTTC
GCCCTGAACCCCTCCCTGCTGGAGACCGCCGAGGGCTGCCAGCAGATCATGGAGCAGCTG
CAGTCCGCCCTGAAGACCTCCGAGGAGCTGAAGTCCCTGTTCAACACCGTGGCCACCCTG
TACTGCGTGCACCAGCGCATCGACGTGAAGGACACCAAGGAGGCCCTGGACAAGATCGAG
GAGATCCAGAACAAGTCCAAGCAGAAGACCCAGCAGGCCGCCGCCGACACCCAGTCCTCC
TCCAAGGTGTCCCAGAACTACGCCCTGAAGCACCGCGCCTACGAGCTGGAATTCGGCATC
AAGGTGAAGCAGCTGTGCAAGCTGCTGCGCGGCGCCAAGGCCCTGACCGACATCGTGACC
CTGACCGAGGAGGCCGAGCTGGAGCTGGCCGAGAACCGCGAGATCCTGAAGGACCCCGTG
CACGGCGTGTACTACGACCCCTCCAAGGACCTGATCGCCGAGATCCAGAAGCAGGGCCAG
GACCAGTGGACCTACCAAATCTACCAGGAGCCCTTCAAGAACCTGAAGACCGGCAAGTAC
GCCCGCAAGCGCTCCGCCCAGACCAACGACGTGAAGCAGCTGGCCGAGGTGGTGCAGAAG
GTGGTGATGGAGTCCATCGTGATCTGGGGCAAGACCCCCAAGTTCCGCCTGCCCATCCAG
AAGGAGACCTGGGAGACCTGGTGGATGGACTACTGGCAGGCCACCTGGATTCCCGAGTGG
GAGTTCGTGAACACCCCACCCCTGGTGAAGCTGTGGTATCAGCTGGAGAAGGACCCCATC
GCCGGCGCCGAGACCTTCTACGTGGACGGCGCCGCCAACCGCGAGACCAAGCTGGGCAAG
GCCGGCTACGTGACCGACCGGGGCCGCCAGAAGGTGGTGTCCCTGACCGAGACCACCAAC
CAGAAGACCGAGCTGCACGTCATCCACCTGGCCCTGCAGGACTCCGGCTCCGAGGTGAAC
ATCGTGACCGACTCCCAGTACGCCCTGGGCATCATCCAGGCCCAGCCCGACAGATCTGAC
CCCGTGGACCCCAACCTGGAGCCCTGGAACCACCCCGGCTCCCAGCCCACCACCCCCGGC
TCCAAGTGCTACTGCAAGGTGTGCTGCTACCACTGCCCCGTGTGCTTCCTGAACAAGGGC
CTGGGCATCTCCTACGGCCGCAAGAAGCGCCGCCAGCGCCGCGGCACCCCCCAGTCCAAC
AAGGACCACCAGAACCCCATCCCCAAGCAGCCCATCCCCCAGACCCAGGGCATCTCCACC
GGCCCCAAGGAGTCCAAGAAGAAGGTGGAGTCCAAGACCGAGACCGACCCCGAGGACGCC
GGCCGCTCCGGCAACTCCGACGAGGAGCTGCTGAAGGCCATCCGCATCATCAAGATCCTG
TACCAGTCCAACCCCTACCCCAAGCCCAAGGGCTCCCGCCAGGCCCGCAAGAACCGCCGC
CGCCGCTGGCGCGCCGGCCAGCGCCAGATCGACTCCCTGTCCGAGCGCATCCTGTCCACC
TGCCTGGGCCGCCCCGCCGAGCCCGTGCCCCTGCAGCTGCCCCCCCTGGAGCTGGACTGC
TCCGAGGACTGCGGCACCTCCGGCACCCAGCAGTCCCAGGGCGCCGAGACCGGCGTGGGC
CGCCCCCAGGTGTCCGTGGAGTCCTCCGCCGTGCTGGGCTCCGGCACCAAGGAGGGTACC
GTGCGCCCCCAGGTGCCCCTGCGCCCCATGACCTACAAGGCCGCCTTCGACCTGTCCTTC
TTTCTGAAGGAGAAGGGCGGCCTGGACGGCCTGATCTACTCCAAGAAGCGCCAGGAGATC
CTGGACCTGTGGGTGTACCACACCCAGGGCTACTTCCCCGACTGGCAGAACTACACCCCC
GGCCCCGGCATCCGCTACCCCCTGACCTTCGGCTGGTGCTTCAAGCTGGTGCCCGTGGAC
CCCGACGAGGTGGAGGAGGCCACCGGCGGCGAGAACAACTCCCTGCTGCACCCCATCTGC
CAGCACGGCATGGACGACGAGGAGAAGGAGACCCTGCGCTGGAAGTTCGACTCCTCCCTG
GCCCTGAAGCACCGCGCCCGCGAACTCCACCCCGAGTCCTACAAGGACTGCCCCCAGATC
ACCCTGTGGCAGCGCCCCCTGGTGACCAAGATCGGCGGCCAGAAGACGCGTGGC
```

Fig.8B(Cont.)

GGCAAGTGGTCCAAGTCCTCCATCGTGGGCTGGCCCGAGGTGCGCGAGCGCATCCGCCAG
ACCCCCACCGCCGCCCGCGAGCGCACCCGCCAGGCCCCCACCGCCGCCAAGGTGGGCGCC
GTGTCCCAGGACCTGGACAAGCACGGCGCCGTGTCCTCCAACGTGAACCACCCCTCCTGC
GCCTGGCTGGAGGCCCAGGAAGAGGAAGAGGTGGGCTTCCCCGAGCTCCTGGACACCGGC
GCCGACGACACCGTGCTGGAGGACATCAACCTGCCCGGCAAGTGGAAGCCCAAGATGATC
GGCGGCATCGGCGGCTTGATCAAGGTGAAGCAGTACGACCAGATCCTGATCGAAATCTGC
GGCAAGAAGGCCATCGGCACCGTGCTGGTGGGCCCCACCCCCGTGAACATCATCGGCCGC
AACATGCTGACCCAGATCGGCTGCACCCTGAACTTCCCCATCTCCCCATCGAGACCGTG
CCCGTGAAGCTGAAGCCCGGCATGGACGGCCCCAAGGTGAAGCAGTGGCCCCTGACCGAG
GAGAAGATCAAGGCCCTGACCGAAATCTGCGCCGACATGGAGAAGGAGGGCAAGATCAGT
AAGATCGGCCCCGAGAACCCCTACAACACCCCCATCTTCGCCATCAAGAAGAAGCAGTCC
ACCAAGTGGCGCAAGCTGGTGGACTTCCGCGAGCTGAACAAGCGCACCCAGGACTTCTGG
GAGGTGCAGCTGGGCATCCCCCACCCCGCCGGCCTGAAGAAGAAAAAGTCCGTGACCGTG
CTGGACGTGGGCGACGCCTACTTCTCCGTGCCCCTGGACGAGTCCTTCCGCAAGTACACC
GCCTTCACCATCCCCTCCACCAACAACGAGACCCCCGGCGTGCGCTACCAGTACAACGTG
CTGCCCCAGGGCTGGAAGGGATCCCCCATCTTCCAGTCCTCCATGACCAAGATCCTGGAG
CCCTTCCGCTCCAAGAACCCCGACATCGTGATCTACCAGTACATGGACGACCTGTACGTG
GGCTCCGACCTGGAGATCGGCCAGCACCGCACCAAGATCGAGGAGCTGCGCGCCCACCTG
CTGTCCTGGGGCTTCATCACCCCCGACAAGAAGCACCAGAAGGAGCCCCCCTTCCTGTGG
ATGGGCTACGAGCTGCACCCCGACAAGTGGACCGTGCAGCCCATCGAGCTGCCCGAGAAG
GACTCCTGGACCGTGAACGACATCCAGAAGCTGGTGGGCAAGCTGAACTGGGCCTCCCAA
ATCTACGCCTGCACCCCCTACGACATCAACCAGATGCTGCGCGGCCCCGGCCGCGCCTTC
GTGACCATCCCCAACCCCCTGCTGGGCCTGGACTA

SEQUENCE LISTING

```
<160> NUMBER OF SEQ ID NOS: 33

<210> SEQ ID NO 1
<211> LENGTH: 11
<212> TYPE: PRT
<213> ORGANISM: Simian immunodeficiency virus

<400> SEQUENCE: 1

Ala Cys Thr Pro Tyr Asp Ile Asn Gln Met Leu
1               5                   10

<210> SEQ ID NO 2
<211> LENGTH: 10
<212> TYPE: PRT
<213> ORGANISM: Human immunodeficiency virus

<400> SEQUENCE: 2

Arg Gly Pro Gly Arg Ala Phe Val Thr Ile
1               5                   10

<210> SEQ ID NO 3
<211> LENGTH: 9
<212> TYPE: PRT
<213> ORGANISM: Human immunodeficiency virus

<400> SEQUENCE: 3

Ala Leu Lys His Arg Ala Tyr Glu Leu
1               5
```

```
<210> SEQ ID NO 4
<211> LENGTH: 9
<212> TYPE: PRT
<213> ORGANISM: Human immunodeficiency virus

<400> SEQUENCE: 4

Pro Pro Ile Pro Val Gly Glu Ile Tyr
1               5

<210> SEQ ID NO 5
<211> LENGTH: 9
<212> TYPE: PRT
<213> ORGANISM: Human immunodeficiency virus

<400> SEQUENCE: 5

Gly Glu Ile Tyr Lys Arg Trp Ile Ile
1               5

<210> SEQ ID NO 6
<211> LENGTH: 10
<212> TYPE: PRT
<213> ORGANISM: Human immunodeficiency virus

<400> SEQUENCE: 6

Lys Arg Trp Ile Ile Leu Gly Leu Asn Lys
1               5                   10

<210> SEQ ID NO 7
<211> LENGTH: 10
<212> TYPE: PRT
<213> ORGANISM: Human immunodeficiency virus

<400> SEQUENCE: 7

Phe Arg Asp Tyr Val Asp Arg Phe Tyr Lys
1               5                   10

<210> SEQ ID NO 8
<211> LENGTH: 11
<212> TYPE: PRT
<213> ORGANISM: Human immunodeficiency virus

<400> SEQUENCE: 8

Arg Asp Tyr Val Asp Arg Phe Tyr Lys Thr Leu
1               5                   10

<210> SEQ ID NO 9
<211> LENGTH: 9
<212> TYPE: PRT
<213> ORGANISM: Human immunodeficiency virus

<400> SEQUENCE: 9

Asp Arg Phe Tyr Lys Thr Leu Arg Ala
1               5

<210> SEQ ID NO 10
<211> LENGTH: 9
<212> TYPE: PRT
<213> ORGANISM: Human immunodeficiency virus

<400> SEQUENCE: 10

Ala Ile Phe Gln Ser Ser Met Thr Lys
1               5

<210> SEQ ID NO 11
<211> LENGTH: 9
<212> TYPE: PRT
```

-continued

<213> ORGANISM: Human immunodeficiency virus

<400> SEQUENCE: 11

Ile Thr Leu Trp Gln Arg Pro Leu Val
1               5

<210> SEQ ID NO 12
<211> LENGTH: 9
<212> TYPE: PRT
<213> ORGANISM: Human immunodeficiency virus

<400> SEQUENCE: 12

Glu Arg Tyr Leu Lys Asp Gln Gln Leu
1               5

<210> SEQ ID NO 13
<211> LENGTH: 8
<212> TYPE: PRT
<213> ORGANISM: Human immunodeficiency virus

<400> SEQUENCE: 13

Tyr Leu Lys Asp Gln Gln Leu Leu
1               5

<210> SEQ ID NO 14
<211> LENGTH: 10
<212> TYPE: PRT
<213> ORGANISM: Human immunodeficiency virus

<400> SEQUENCE: 14

Thr Val Tyr Tyr Gly Val Pro Val Trp Lys
1               5                   10

<210> SEQ ID NO 15
<211> LENGTH: 11
<212> TYPE: PRT
<213> ORGANISM: Human immunodeficiency virus

<400> SEQUENCE: 15

Arg Pro Gln Val Pro Leu Arg Pro Met Thr Tyr
1               5                   10

<210> SEQ ID NO 16
<211> LENGTH: 10
<212> TYPE: PRT
<213> ORGANISM: Human immunodeficiency virus

<400> SEQUENCE: 16

Gln Val Pro Leu Arg Pro Met Thr Tyr Lys
1               5                   10

<210> SEQ ID NO 17
<211> LENGTH: 8
<212> TYPE: PRT
<213> ORGANISM: Human immunodeficiency virus

<400> SEQUENCE: 17

Val Pro Leu Arg Pro Met Thr Tyr
1               5

<210> SEQ ID NO 18
<211> LENGTH: 9
<212> TYPE: PRT
<213> ORGANISM: Human immunodeficiency virus

<400> SEQUENCE: 18

Ala Val Asp Leu Ser His Phe Leu Lys
1               5

<210> SEQ ID NO 19
<211> LENGTH: 9
<212> TYPE: PRT
<213> ORGANISM: Human immunodeficiency virus

<400> SEQUENCE: 19

Asp Leu Ser His Phe Leu Lys Glu Lys
1               5

<210> SEQ ID NO 20
<211> LENGTH: 8
<212> TYPE: PRT
<213> ORGANISM: Human immunodeficiency virus

<400> SEQUENCE: 20

Phe Leu Lys Glu Lys Gly Gly Leu
1               5

<210> SEQ ID NO 21
<211> LENGTH: 9
<212> TYPE: PRT
<213> ORGANISM: Human immunodeficiency virus

<400> SEQUENCE: 21

Ile Leu Lys Glu Pro Val His Gly Val
1               5

<210> SEQ ID NO 22
<211> LENGTH: 10
<212> TYPE: PRT
<213> ORGANISM: Human immunodeficiency virus

<400> SEQUENCE: 22

Ile Leu Lys Glu Pro Val His Gly Val Tyr
1               5                   10

<210> SEQ ID NO 23
<211> LENGTH: 9
<212> TYPE: PRT
<213> ORGANISM: Human immunodeficiency virus

<400> SEQUENCE: 23

His Pro Asp Ile Val Ile Tyr Gln Tyr
1               5

<210> SEQ ID NO 24
<211> LENGTH: 9
<212> TYPE: PRT
<213> ORGANISM: Human immunodeficiency virus

<400> SEQUENCE: 24

Val Ile Tyr Gln Tyr Met Asp Asp Leu
1               5

<210> SEQ ID NO 25
<211> LENGTH: 10
<212> TYPE: PRT
<213> ORGANISM: Human immunodeficiency virus

<400> SEQUENCE: 25

Thr Pro Gly Pro Gly Val Arg Tyr Pro Leu
1               5                   10

<210> SEQ ID NO 26
<211> LENGTH: 527
<212> TYPE: PRT
<213> ORGANISM: Artificial Sequence
<220> FEATURE:
<223> OTHER INFORMATION: Description of Artificial Sequence: Synthetic chimeric polypeptide sequence

<400> SEQUENCE: 26

```
Met Pro Ile Val Gln Asn Ala Gln Gly Gln Met His Gln Ala Leu Ser
1               5                   10                  15

Pro Arg Thr Leu Asn Ala Trp Val Lys Val Ile Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Met Met Leu Asn Ile Val Gly Gly His Gln Ala
    50                  55                  60

Ala Met Gln Met Leu Lys Asp Thr Ile Asn Glu Glu Ala Ala Glu Trp
65                  70                  75                  80

Asp Arg Leu His Pro Val His Ala Gly Pro Ile Pro Pro Gly Gln Met
                85                  90                  95

Arg Glu Pro Arg Gly Ser Asp Ile Ala Gly Thr Thr Ser Thr Leu Gln
            100                 105                 110

Glu Gln Ile Gly Trp Met Thr Ser Asn Pro Pro Ile Pro Val Gly Asp
        115                 120                 125

Ile Tyr Lys Arg Trp Ile Ile Leu Gly Leu Asn Lys Ile Val Arg Met
    130                 135                 140

Tyr Ser Pro Val Ser Ile Leu Asp Ile Arg Gln Gly Pro Lys Glu Pro
145                 150                 155                 160

Phe Arg Asp Tyr Val Asp Arg Phe Phe Lys Thr Leu Arg Ala Glu Gln
                165                 170                 175

Ala Thr Gln Glu Val Lys Asn Trp Met Thr Glu Thr Leu Leu Val Gln
            180                 185                 190

Asn Ala Asn Pro Asp Cys Lys Ser Ile Leu Arg Ala Leu Gly Pro Gly
        195                 200                 205

Ala Thr Leu Glu Glu Met Met Thr Ala Cys Gln Gly Val Gly Gly Pro
    210                 215                 220

Gly His Lys Ala Arg Val Leu Gly Thr Gly Ala Arg Ala Ser Val Leu
225                 230                 235                 240

Ser Gly Gly Lys Leu Asp Ala Trp Glu Lys Ile Arg Leu Arg Pro Gly
                245                 250                 255

Gly Lys Lys Lys Tyr Arg Leu Lys His Leu Val Trp Ala Ser Arg Glu
            260                 265                 270

Leu Glu Arg Phe Ala Leu Asn Pro Ser Leu Leu Glu Thr Ala Glu Gly
        275                 280                 285

Cys Gln Gln Ile Met Glu Gln Leu Gln Ser Ala Leu Lys Thr Ser Glu
    290                 295                 300

Glu Leu Lys Ser Leu Phe Asn Thr Val Ala Thr Leu Tyr Cys Val His
305                 310                 315                 320

Gln Arg Ile Asp Val Lys Asp Thr Lys Glu Ala Leu Asp Lys Ile Glu
                325                 330                 335

Glu Ile Gln Asn Lys Ser Lys Gln Lys Thr Gln Gln Ala Ala Ala Asp
            340                 345                 350

Thr Gln Ser Ser Ser Lys Val Ser Gln Asn Tyr Ala Leu Lys His Arg
        355                 360                 365
```

```
Ala Tyr Glu Leu Glu Phe Pro Pro Ile Pro Val Gly Glu Ile Tyr Lys
    370                 375                 380

Arg Trp Ile Ile Phe Arg Asp Tyr Val Asp Arg Phe Tyr Lys Thr Leu
385                 390                 395                 400

Arg Ala Ile Phe Gln Ser Ser Met Thr Lys Ile Thr Leu Trp Gln Arg
                405                 410                 415

Pro Leu Val Glu Arg Tyr Leu Lys Asp Gln Gln Leu Leu Thr Val Tyr
            420                 425                 430

Tyr Gly Val Pro Val Trp Lys Arg Pro Gln Val Pro Leu Arg Pro Met
        435                 440                 445

Thr Tyr Lys Ala Val Asp Leu Ser His Phe Leu Lys Glu Lys Gly Gly
    450                 455                 460

Leu Ile Leu Lys Glu Pro Val His Gly Val Tyr His Pro Asp Ile Val
465                 470                 475                 480

Ile Tyr Gln Tyr Met Asp Asp Leu Thr Pro Gly Pro Gly Val Arg Tyr
                485                 490                 495

Pro Leu Ala Cys Thr Pro Tyr Asp Ile Asn Gln Met Leu Arg Gly Pro
            500                 505                 510

Gly Arg Ala Phe Val Thr Ile Pro Asn Pro Leu Leu Gly Leu Asp
        515                 520                 525

<210> SEQ ID NO 27
<211> LENGTH: 1608
<212> TYPE: DNA
<213> ORGANISM: Artificial Sequence
<220> FEATURE:
<223> OTHER INFORMATION: Description of Artificial Sequence: Synthetic
      chimeric polynucleotide sequence

<400> SEQUENCE: 27
aagcttcccg ccgccaccat gcccatcgtg cagaacgccc agggccagat gcaccaggcc      60
ctgtcccccc gcaccctgaa cgcctgggtg aaggtgatcg aggagaaggc cttctccccc     120
gaggtgatcc ccatgttctc cgccctgtcc gagggcgcca ccccccagga cctgaacatg     180
atgctgaaca tcgtgggcgg ccaccaggcc gccatgcaga tgctgaagga caccatcaac     240
gaggaggccg ccgagtggga ccgcctgcac cccgtgcacg ccggccccat ccccccoggc     300 cagatgcgcg agccccgcgg atccgacatc gccggcacca cctccaccct gcaggagcag     360
atcggctgga tgacctccaa ccccccccatc cccgtgggcg acatctacaa gcgctggatc     420
atcctgggcc tgaacaagat cgtacgcatg tactcccccg tgtccatcct ggacatccgc     480
cagggccccc aggagccctt ccgcgactac gtggaccgct tcttcaagac cctgcgcgcc     540
gagcaggcca cccaggaggt gaagaactgg atgaccgaga ccctgctggt gcagaacgcc     600
aaccccgact gcaagtccat cctgcgcgcc ctgggccccg cgccacccct ggaggagatg     660
atgaccgcct gccagggcgt gggcggcccc ggccacaagg cccgcgtgct gggtaccggc     720
gcccgcgcct ccgtgctgtc cggcggcaag ctggacgcct gggagaagat ccgcctgcgc     780
cccggcggca agaagaagta ccgcctgaag cacctggtgt gggcctcccg cgagctggag     840
cgcttcgccc tgaacccctc cctgctggag accgccgagg ctgccagca gatcatggag     900 cagctgcagt ccgccctgaa gacctccgag gagctgaagt ccctgttcaa caccgtggcc     960
accctgtact gcgtgcacca gcgcatcgac gtgaaggaca ccaaggaggc cctggacaag    1020
atcgaggaga tccagaacaa gtccaagcag aagacccagc aggccgccgc cgacacccag    1080
tcctcctcca aggtgtccca gaactacgcc ctgaagcacc gcgcctacga gctggaattc    1140
```

```
cctccaattc ctgtcgggga gatttataaa cggtggatca ttttagggga ttatgtcgat    1200
aggttttata aaacgctcag ggccatcttc cagtcctcca tgaccaagat caccctgtgg    1260
cagcgccccc tggtggagcg ctacctgaag gaccagcagc tgctgaccgt gtactacggc    1320
gtgcccgtgt ggaagcgccc ccaggtgccc ctgcgcccca tgacctacaa ggccgtggac    1380
ctgtcccact tcctgaagga agggcggc ctgatcctga aggagcccgt gcacggcgtg    1440 taccacccg acatcgtgat ctaccagtac atggacgacc tgaccccgg ccccggcgtg    1500 cgctacccc tggcctgcac ccctacgac atcaaccaga tgctgcgcgg ccccggccgc    1560
gccttcgtga ccatccccaa ccccctgctg ggcctggact gatctaga               1608
```

<210> SEQ ID NO 28
<211> LENGTH: 633
<212> TYPE: PRT
<213> ORGANISM: Artificial Sequence
<220> FEATURE:
<223> OTHER INFORMATION: Description of Artificial Sequence: Synthetic chimeric polypeptide sequence

<400> SEQUENCE: 28

```
Met Pro Ile Val Gln Asn Ala Gln Gly Gln Met His Gln Ala Leu Ser
1               5                   10                  15

Pro Arg Thr Leu Asn Ala Trp Val Lys Val Ile Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Met Met Leu Asn Ile Val Gly Gly His Gln Ala
    50                  55                  60

Ala Met Gln Met Leu Lys Asp Thr Ile Asn Glu Glu Ala Ala Glu Trp
65                  70                  75                  80

Asp Arg Leu His Pro Val His Ala Gly Pro Ile Pro Gly Gln Met
                85                  90                  95

Arg Glu Pro Arg Gly Ser Asp Ile Ala Gly Thr Thr Ser Thr Leu Gln
            100                 105                 110

Glu Gln Ile Gly Trp Met Thr Ser Asn Pro Pro Ile Pro Val Gly Asp
        115                 120                 125

Ile Tyr Lys Arg Trp Ile Ile Leu Gly Leu Asn Lys Ile Val Arg Met
    130                 135                 140

Tyr Ser Pro Val Ser Ile Leu Asp Ile Arg Gln Gly Pro Lys Glu Pro
145                 150                 155                 160

Phe Arg Asp Tyr Val Asp Arg Phe Phe Lys Thr Leu Arg Ala Glu Gln
                165                 170                 175

Ala Thr Gln Glu Val Lys Asn Trp Met Thr Glu Thr Leu Leu Val Gln
            180                 185                 190

Asn Ala Asn Pro Asp Cys Lys Ser Ile Leu Arg Ala Leu Gly Pro Gly
        195                 200                 205

Ala Thr Leu Glu Glu Met Met Thr Ala Cys Gln Gly Val Gly Gly Pro
    210                 215                 220

Gly His Lys Ala Arg Val Leu Gly Thr Ala Arg Ala Ser Val Leu
225                 230                 235                 240

Ser Gly Gly Lys Leu Asp Ala Trp Glu Lys Ile Arg Leu Arg Pro Gly
                245                 250                 255

Gly Lys Lys Lys Tyr Arg Leu Lys His Leu Val Trp Ala Ser Arg Glu
            260                 265                 270

Leu Glu Arg Phe Ala Leu Asn Pro Ser Leu Leu Glu Thr Ala Glu Gly
        275                 280                 285
```

```
Cys Gln Gln Ile Met Glu Gln Leu Gln Ser Ala Leu Lys Thr Ser Glu
    290                 295                 300

Glu Leu Lys Ser Leu Phe Asn Thr Val Ala Thr Leu Tyr Cys Val His
305                 310                 315                 320

Gln Arg Ile Asp Val Lys Asp Thr Lys Glu Ala Leu Asp Lys Ile Glu
                325                 330                 335

Glu Ile Gln Asn Lys Ser Lys Gln Lys Thr Gln Gln Ala Ala Ala Asp
                340                 345                 350

Thr Gln Ser Ser Ser Lys Val Ser Gln Asn Tyr Ala Leu Lys His Arg
        355                 360                 365

Ala Tyr Glu Leu Glu Phe Met Ala Thr Thr Met Asp Pro Val Asp Pro
    370                 375                 380

Asn Leu Glu Pro Trp Asn His Pro Gly Ser Gln Pro Thr Thr Pro Gly
385                 390                 395                 400

Ser Lys Cys Tyr Cys Lys Val Cys Cys Tyr His Cys Pro Val Cys Phe
                405                 410                 415

Leu Asn Lys Gly Leu Gly Ile Ser Tyr Gly Arg Lys Lys Arg Arg Gln
                420                 425                 430

Arg Arg Gly Thr Pro Gln Ser Asn Lys Asp His Gln Asn Pro Ile Pro
        435                 440                 445

Lys Gln Pro Ile Pro Gln Thr Gln Gly Ile Ser Thr Gly Pro Lys Glu
    450                 455                 460

Ser Lys Lys Lys Val Glu Ser Lys Thr Glu Thr Asp Pro Glu Glu Phe
465                 470                 475                 480

Pro Pro Ile Pro Val Gly Glu Ile Tyr Lys Arg Trp Ile Ile Phe Arg
                485                 490                 495

Asp Tyr Val Asp Arg Phe Tyr Lys Thr Leu Arg Ala Ile Phe Gln Ser
                500                 505                 510

Ser Met Thr Lys Ile Thr Leu Trp Gln Arg Pro Leu Val Glu Arg Tyr
        515                 520                 525

Leu Lys Asp Gln Gln Leu Leu Thr Val Tyr Tyr Gly Val Pro Val Trp
    530                 535                 540

Lys Arg Pro Gln Val Pro Leu Arg Pro Met Thr Tyr Lys Ala Val Asp
545                 550                 555                 560

Leu Ser His Phe Leu Lys Glu Lys Gly Gly Leu Ile Leu Lys Glu Pro
                565                 570                 575

Val His Gly Val Tyr His Pro Asp Ile Val Ile Tyr Gln Tyr Met Asp
                580                 585                 590

Asp Leu Thr Pro Gly Pro Gly Val Arg Tyr Pro Leu Ala Cys Thr Pro
        595                 600                 605

Tyr Asp Ile Asn Gln Met Leu Arg Gly Pro Gly Arg Ala Phe Val Thr
    610                 615                 620

Ile Pro Asn Pro Leu Leu Gly Leu Asp
625                 630

<210> SEQ ID NO 29
<211> LENGTH: 1914
<212> TYPE: DNA
<213> ORGANISM: Artificial Sequence
<220> FEATURE:
<223> OTHER INFORMATION: Description of Artificial Sequence: Synthetic
      chimeric polynucleotide sequence

<400> SEQUENCE: 29
cccgccgcca ccatgcccat cgtgcagaac gcccagggcc agatgcacca ggccctgtcc    60
```

```
cccccgcaccc tgaacgcctg ggtgaaggtg atcgaggaga aggccttctc ccccgaggtg       120
atccccatgt tctccgccct gtccgagggc gccacccccc aggacctgaa catgatgctg       180
aacatcgtgg gcggccacca ggccgccatg cagatgctga aggacaccat caacgaggag       240
gccgccgagt gggaccgcct gcaccccgtg cacgccggcc catcccccc cggccagatg        300 cgcgagcccc gcggatccga catcgccggc accacctcca ccctgcagga gcagatcggc      360
tggatgacct ccaaccccc catccccgtg gcgacatct acaagcgctg atcatcctg         420 ggcctgaaca agatcgtgcg catgtactcc cccgtgtcca tcctggacat ccgccagggc      480
cccaaggagc cttccgcga ctacgtggac cgcttcttca gaccctgcg cgccgagcag        540 gccacccagg aggtgaagaa ctggatgacc gagaccctgc tggtgcagaa cgccaacccc     600
gactgcaagt ccatcctgcg cgccctgggc cccggcgcca ccctggagga gatgatgacc      660
gcctgccagg gcgtgggcgg ccccggccac aaggcccgcg tgctgggtac cggcgcccgc      720
gcctccgtgc tgtccggcgg caagctggac gcctgggaga gatccgcct gcgcccccgg      780 ggcaagaaga agtaccgcct gaagcacctg gtgtgggcct cccgcgagct ggagcgcttc     840
gccctgaacc cctccctgct ggagaccgcc gagggctgcc agcagatcat ggagcagctg      900
cagtccgccc tgaagacctc cgaggagctg aagtccctgt tcaacaccgt ggccaccctg      960
tactgcgtgc accagcgcat cgacgtgaag gacaccaagg aggccctgga caagatcgag     1020
gagatccaga acaagtccaa gcagaagacc cagcaggccg ccgccgacac ccagtcctcc     1080
tccaaggtgt cccagaacta cgccctgaag caccgcgcct acgagctgga attcatggcc     1140
acaaccatgg acccgtgga ccccaacctg gagccctgga ccaccccgg ctcccagccc      1200 accaccccg gctccaagtg ctactgcaag gtgtgctgct accactgccc cgtgtgcttc     1260
ctgaacaagg gcctgggcat ctcctacggc cgcaagaagc gccgccagcg ccgcggcacc      1320
ccccagtcca acaaggacca ccagaacccc atccccaagc agcccatccc ccagacccag      1380
ggcatctcca ccggtcccaa ggagtccaag aagaaggtgg agtccaagac cgagaccgac      1440
cccgaggaat ccctccaat tcctgtcggg gagattata acggtggat catttttagg       1500 gattatgtcg ataggttttta taaaacgctc agggccatct tccagtcctc catgaccaag      1560
atcaccctgt ggcagcgccc cctggtggag cgctacctga aggaccagca gctgctgacc     1620
gtgtactacg gcgtgcccgt gtggaagcgc ccccaggtgc ccctgcgccc catgacctac      1680
aaggccgtgg acctgtccca cttcctgaag gagaagggcg gcctgatcct gaaggagccc      1740
gtgcacggcg tgtaccaccc cgacatcgtg atctaccagt acatggacga cctgaccccc     1800
ggccccggcg tgcgctaccc cctggcctgc acccccctacg acatcaacca gatgctgcgc    1860
ggccccggcc gcgccttcgt gaccatcccc aaccccctgc tgggcctgga ctga           1914
```

<210> SEQ ID NO 30
<211> LENGTH: 104
<212> TYPE: PRT
<213> ORGANISM: Artificial Sequence
<220> FEATURE:
<223> OTHER INFORMATION: Description of Artificial Sequence: Synthetic chimeric polypeptide sequence

<400> SEQUENCE: 30

Met Ala Thr Thr Met Asp Pro Val Asp Pro Asn Leu Glu Pro Trp Asn
1               5                   10                  15

His Pro Gly Ser Gln Pro Thr Thr Pro Gly Ser Lys Cys Tyr Cys Lys
            20                  25                  30

Val Cys Cys Tyr His Cys Pro Val Cys Phe Leu Asn Lys Gly Leu Gly

```
                35                  40                  45
Ile Ser Tyr Gly Arg Lys Lys Arg Arg Gln Arg Gly Thr Pro Gln
 50                  55                  60

Ser Asn Lys Asp His Gln Asn Pro Ile Pro Lys Gln Pro Ile Pro Gln
 65                  70                  75                  80

Thr Gln Gly Ile Ser Thr Gly Pro Lys Glu Ser Lys Lys Val Glu
             85                  90                  95

Ser Lys Thr Glu Thr Asp Pro Glu
            100
```

<210> SEQ ID NO 31
<211> LENGTH: 2493
<212> TYPE: DNA
<213> ORGANISM: Artificial Sequence
<220> FEATURE:
<223> OTHER INFORMATION: Description of Artificial Sequence: Synthetic chimeric polynucleotide sequence

<400> SEQUENCE: 31

| | | | | | |
|---|---|---|---|---|---|
| cccgccgcca | ccatgcccat | cgtgcagaac | gcccagggcc | agatgcacca | ggccctgtcc | 60 |
| ccccgcaccc | tgaacgcctg | ggtgaaggtg | atcgaggaga | aggccttctc | ccccgaggtg | 120 |
| atccccatgt | tctccgccct | gtccgagggc | gccacccccc | aggacctgaa | catgatgctg | 180 |
| aacatcgtgg | gcggccacca | ggccgccatg | cagatgctga | aggacaccat | caacgaggag | 240 |
| gccgccgagt | gggaccgcct | gcaccccgtg | cacgccggcc | catccccccc | cggccagatg | 300 |
| cgcgagcccc | gcggatccga | catcgccggc | accacctcca | ccctgcagga | gcagatcggc | 360 |
| tggatgacct | ccaaccccc | catccccgtg | ggcgacatct | acaagcgctg | gatcatcctg | 420 |
| ggcctgaaca | agatcgtgcg | catgtactcc | ccgtgtcca | tcctggacat | ccgccagggc | 480 |
| cccaaggagc | ccttccgcga | ctacgtggac | cgcttcttca | agaccctgcg | cgccgagcag | 540 |
| gccacccagg | aggtgaagaa | ctggatgacc | gagaccctgc | tggtgcagaa | cgccaacccc | 600 |
| gactgcaagt | ccatcctgcg | cgccctgggc | cccggcgcca | cctggaggac | gatgatgacc | 660 |
| gcctgccagg | gcgtgggcgg | ccccggccac | aaggcccgcg | tgctgggtac | cggcgcccgc | 720 |
| gcctccgtgc | tgtccggcgg | caagctggac | gcctgggaga | gatccgcct | cgcccccggc | 780 |
| ggcaagaaga | agtaccgcct | gaagcacctg | gtgtgggcct | ccgcgagct | ggagcgcttc | 840 |
| gccctgaacc | cctccctgct | ggagaccgcc | gagggctgcc | agcagatcat | ggagcagctg | 900 |
| cagtccgccc | tgaagacctc | cgaggagctg | aagtccctgt | tcaacaccgt | ggccaccctg | 960 |
| tactgcgtgc | accagcgcat | cgacgtgaag | gacaccaagg | aggccctgga | caagatcgag | 1020 |
| gagatccaga | acaagtccaa | gcagaagacc | cagcaggccg | ccgccgacac | ccagtcctcc | 1080 |
| tccaaggtgt | cccagaacta | cgccctgaag | caccgcgcct | acgagctgga | attccctcca | 1140 |
| attcctgtcg | gggagattta | taacggtgg | atcattttta | gggattatgt | cgataggttt | 1200 |
| tataaacgc | tcagggccat | cttccagtcc | tccatgacca | agatcaccct | gtggcagcgc | 1260 |
| cccctggtgg | agcgctacct | gaaggaccag | cagctgctga | ccgtgtacta | cggcgtgccc | 1320 |
| gtgtggaagc | gccccaggt | gcccctgcgc | cccatgacct | acaaggccgt | ggacctgtcc | 1380 |
| cacttcctga | aggagaaggg | cggcctgatc | ctgaaggagc | ccgtgcacgg | cgtgtaccac | 1440 |
| cccgacatcg | tgatctacca | gtacatggac | gacctgaccc | ccggcccgg | cgtgcgctac | 1500 |
| cccctggcct | gcacccccta | cgacatcaac | cagatgctgc | gcggcccgg | ccgcgccttc | 1560 |
| gtgaccatcc | ccaacccct | gctgggcctg | gactgagcgg | ccgcccctct | ccctcccccc | 1620 |
| ccctaacgt | tactggccga | agccgcttgg | aataaggccg | gtgtgcgttt | gtctatatgt | 1680 |

```
tattttccac catattgccg tcttttggca atgtgagggc ccggaaacct ggccctgtct    1740
tcttgacgag cattcctagg ggtctttccc ctctcgccaa aggaatgcaa ggtctgttga    1800
atgtcgtgaa ggaagcagtt cctctggaag cttcttgaag acaaacaacg tctgtagcga    1860 cccctttgcag gcagcggaac cccccacctg gcgacaggtg cctctgcggc caaaagccac   1920
gtgtataaga tacacctgca aaggcggcac aaccccagtg ccacgttgtg agttggatag    1980
ttgtggaaag agtcaaatgg ctctcctcaa gcgtattcaa caaggggctg aaggatgccc    2040
agaaggtacc ccattgtatg ggatctgatc tggggcctcg gtgcacatgc tttacatgtg    2100
tttagtcgag gttaaaaaaa cgtctaggcc ccccgaacca cggggacgtg gttttccttt    2160
gaaaaacacg atgataatat ggccacaacc atggaccccg tggacccccaa cctggagccc   2220 tggaaccacc ccggctccca gcccaccacc cccggctcca gtgctactg caaggtgtgc     2280 tgctaccact gccccgtgtg cttcctgaac aagggcctgg gcatctccta cggccgcaag    2340
aagcgccgcc agcgccgcgg cacccccag tccaacaagg accaccagaa ccccatcccc     2400
aagcagccca tccccagac ccagggcatc tccaccggcc caaggagtc aagaagaag        2460 gtggagtcca gaccgagac cgaccccgag taa                                   2493
```

<210> SEQ ID NO 32
<211> LENGTH: 1445
<212> TYPE: PRT
<213> ORGANISM: Artificial Sequence
<220> FEATURE:
<223> OTHER INFORMATION: Description of Artificial Sequence: Synthetic
      chimeric polypeptide sequence

<400> SEQUENCE: 32

```
Met Pro Ile Val Gln Asn Ala Gln Gly Gln Met His Gln Ala Leu Ser
1               5                   10                  15

Pro Arg Thr Leu Asn Ala Trp Val Lys Val Ile Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Met Met Leu Asn Ile Val Gly Gly His Gln Ala
    50                  55                  60

Ala Met Gln Met Leu Lys Asp Thr Ile Asn Glu Glu Ala Ala Glu Trp
65                  70                  75                  80

Asp Arg Leu His Pro Val His Ala Gly Pro Ile Pro Pro Gly Gln Met
                85                  90                  95

Arg Glu Pro Arg Gly Ser Asp Ile Ala Gly Thr Thr Ser Thr Leu Gln
            100                 105                 110

Glu Gln Ile Gly Trp Met Thr Ser Asn Pro Pro Ile Pro Val Gly Asp
        115                 120                 125

Ile Tyr Lys Arg Trp Ile Ile Leu Gly Leu Asn Lys Ile Val Arg Met
    130                 135                 140

Tyr Ser Pro Val Ser Ile Leu Asp Ile Arg Gln Gly Pro Lys Glu Pro
145                 150                 155                 160

Phe Arg Asp Tyr Val Asp Arg Phe Phe Lys Thr Leu Arg Ala Glu Gln
                165                 170                 175

Ala Thr Gln Glu Val Lys Asn Trp Met Thr Glu Thr Leu Leu Val Gln
            180                 185                 190

Asn Ala Asn Pro Asp Cys Lys Ser Ile Leu Arg Ala Leu Gly Pro Gly
        195                 200                 205

Ala Thr Leu Glu Glu Met Met Thr Ala Cys Gln Gly Val Gly Gly Pro
```

-continued

```
            210                 215                 220
Gly His Lys Ala Arg Val Leu Gly Thr Gly Ala Arg Ala Ser Val Leu
225                 230                 235                 240

Ser Gly Gly Lys Leu Asp Ala Trp Glu Lys Ile Arg Leu Arg Pro Gly
                245                 250                 255

Gly Lys Lys Lys Tyr Arg Leu Lys His Leu Val Trp Ala Ser Arg Glu
                260                 265                 270

Leu Glu Arg Phe Ala Leu Asn Pro Ser Leu Leu Glu Thr Ala Glu Gly
                275                 280                 285

Cys Gln Gln Ile Met Glu Gln Leu Gln Ser Ala Leu Lys Thr Ser Glu
290                 295                 300

Glu Leu Lys Ser Leu Phe Asn Thr Val Ala Thr Leu Tyr Cys Val His
305                 310                 315                 320

Gln Arg Ile Asp Val Lys Asp Thr Lys Glu Ala Leu Asp Lys Ile Glu
                325                 330                 335

Glu Ile Gln Asn Lys Ser Lys Gln Lys Thr Gln Gln Ala Ala Ala Asp
                340                 345                 350

Thr Gln Ser Ser Ser Lys Val Ser Gln Asn Tyr Ala Leu Lys His Arg
                355                 360                 365

Ala Tyr Glu Leu Glu Phe Gly Ile Lys Val Lys Gln Leu Cys Lys Leu
370                 375                 380

Leu Arg Gly Ala Lys Ala Leu Thr Asp Ile Val Thr Leu Thr Glu Glu
385                 390                 395                 400

Ala Glu Leu Glu Leu Ala Glu Asn Arg Glu Ile Leu Lys Asp Pro Val
                405                 410                 415

His Gly Val Tyr Tyr Asp Pro Ser Lys Asp Leu Ile Ala Glu Ile Gln
                420                 425                 430

Lys Gln Gly Gln Asp Gln Trp Thr Tyr Gln Ile Tyr Gln Glu Pro Phe
                435                 440                 445

Lys Asn Leu Lys Thr Gly Lys Tyr Ala Arg Lys Ser Ala Gln Thr
450                 455                 460

Asn Asp Val Lys Gln Leu Ala Glu Val Val Gln Lys Val Val Met Glu
465                 470                 475                 480

Ser Ile Val Ile Trp Gly Lys Thr Pro Lys Phe Arg Leu Pro Ile Gln
                485                 490                 495

Lys Glu Thr Trp Glu Thr Trp Trp Met Asp Tyr Trp Gln Ala Thr Trp
                500                 505                 510

Ile Pro Glu Trp Glu Phe Val Asn Thr Pro Pro Leu Val Lys Leu Trp
                515                 520                 525

Tyr Gln Leu Glu Lys Asp Pro Ile Ala Gly Ala Glu Thr Phe Tyr Val
530                 535                 540

Asp Gly Ala Ala Asn Arg Glu Thr Lys Leu Gly Lys Ala Gly Tyr Val
545                 550                 555                 560

Thr Asp Arg Gly Arg Gln Lys Val Val Ser Leu Thr Glu Thr Thr Asn
                565                 570                 575

Gln Lys Thr Glu Leu His Val Ile His Leu Ala Leu Gln Asp Ser Gly
                580                 585                 590

Ser Glu Val Asn Ile Val Thr Asp Ser Gln Tyr Ala Leu Gly Ile Ile
                595                 600                 605

Gln Ala Gln Pro Asp Arg Ser Asp Pro Val Asp Asn Leu Glu Pro
610                 615                 620

Trp Asn His Pro Gly Ser Gln Pro Thr Thr Pro Gly Ser Lys Cys Tyr
625                 630                 635                 640
```

-continued

```
Cys Lys Val Cys Cys Tyr His Cys Pro Val Cys Phe Leu Asn Lys Gly
            645                 650                 655
Leu Gly Ile Ser Tyr Gly Arg Lys Arg Arg Gln Arg Arg Gly Thr
        660                 665                 670
Pro Gln Ser Asn Lys Asp His Gln Asn Pro Ile Pro Lys Gln Pro Ile
            675                 680                 685
Pro Gln Thr Gln Gly Ile Ser Thr Gly Pro Lys Glu Ser Lys Lys
    690                 695                 700
Val Glu Ser Lys Thr Glu Thr Asp Pro Glu Asp Ala Gly Arg Ser Gly
705                 710                 715                 720
Asn Ser Asp Glu Glu Leu Leu Lys Ala Ile Arg Ile Ile Lys Ile Leu
                725                 730                 735
Tyr Gln Ser Asn Pro Tyr Pro Lys Pro Lys Gly Ser Arg Gln Ala Arg
            740                 745                 750
Lys Asn Arg Arg Arg Arg Trp Arg Ala Gly Gln Arg Gln Ile Asp Ser
        755                 760                 765
Leu Ser Glu Arg Ile Leu Ser Thr Cys Leu Gly Arg Pro Ala Glu Pro
770                 775                 780
Val Pro Leu Gln Leu Pro Pro Leu Glu Leu Asp Cys Ser Glu Asp Cys
785                 790                 795                 800
Gly Thr Ser Gly Thr Gln Gln Ser Gln Gly Ala Glu Thr Gly Val Gly
            805                 810                 815
Arg Pro Gln Val Ser Val Glu Ser Ser Ala Val Leu Gly Ser Gly Thr
            820                 825                 830
Lys Glu Gly Thr Val Arg Pro Gln Val Pro Leu Arg Pro Met Thr Tyr
            835                 840                 845
Lys Ala Ala Phe Asp Leu Ser Phe Phe Leu Lys Glu Lys Gly Gly Leu
    850                 855                 860
Asp Gly Leu Ile Tyr Ser Lys Lys Arg Gln Glu Ile Leu Asp Leu Trp
865                 870                 875                 880
Val Tyr His Thr Gln Gly Tyr Phe Pro Asp Trp Gln Asn Tyr Thr Pro
            885                 890                 895
Gly Pro Gly Ile Arg Tyr Pro Leu Thr Phe Gly Trp Cys Phe Lys Leu
        900                 905                 910
Val Pro Val Asp Pro Asp Glu Val Glu Glu Ala Thr Gly Gly Glu Asn
            915                 920                 925
Asn Ser Leu Leu His Pro Ile Cys Gln His Gly Met Asp Asp Glu Glu
    930                 935                 940
Lys Glu Thr Leu Arg Trp Lys Phe Asp Ser Ser Leu Ala Leu Lys His
945                 950                 955                 960
Arg Ala Arg Glu Leu His Pro Glu Ser Tyr Lys Asp Cys Pro Gln Ile
            965                 970                 975
Thr Leu Trp Gln Arg Pro Leu Val Thr Lys Ile Gly Gly Gln Lys Thr
            980                 985                 990
Arg Gly Gly Lys Trp Ser Lys Ser  Ser Ile Val Gly Trp Pro Glu Val
        995                 1000                1005
Arg Glu  Arg Ile Arg Gln Thr  Pro Thr Ala Ala Arg  Glu Arg Thr
    1010                1015                1020
Arg Gln Ala Pro Thr Ala Ala  Lys Val Gly Ala Val  Ser Gln Asp
        1025                1030                1035
Leu Asp Lys His Gly Ala Val  Ser Ser Asn Val Asn  His Pro Ser
    1040                1045                1050
Cys Ala Trp Leu Glu Ala Gln  Glu Glu Glu Glu Val  Gly Phe Pro
        1055                1060                1065
```

```
Glu Leu Leu Asp Thr Gly Ala Asp Asp Thr Val Leu Glu Asp Ile
    1070            1075            1080

Asn Leu Pro Gly Lys Trp Lys Pro Lys Met Ile Gly Gly Ile Gly
    1085            1090            1095

Gly Leu Ile Lys Val Lys Gln Tyr Asp Gln Ile Leu Ile Glu Ile
    1100            1105            1110

Cys Gly Lys Lys Ala Ile Gly Thr Val Leu Val Gly Pro Thr Pro
    1115            1120            1125

Val Asn Ile Ile Gly Arg Asn Met Leu Thr Gln Ile Gly Cys Thr
    1130            1135            1140

Leu Asn Phe Pro Ile Ser Pro Ile Glu Thr Val Pro Val Lys Leu
    1145            1150            1155

Lys Pro Gly Met Asp Gly Pro Lys Val Lys Gln Trp Pro Leu Thr
    1160            1165            1170

Glu Glu Lys Ile Lys Ala Leu Thr Glu Ile Cys Ala Asp Met Glu
    1175            1180            1185

Lys Glu Gly Lys Ile Ser Lys Ile Gly Pro Glu Asn Pro Tyr Asn
    1190            1195            1200

Thr Pro Ile Phe Ala Ile Lys Lys Lys Gln Ser Thr Lys Trp Arg
    1205            1210            1215

Lys Leu Val Asp Phe Arg Glu Leu Asn Lys Arg Thr Gln Asp Phe
    1220            1225            1230

Trp Glu Val Gln Leu Gly Ile Pro His Pro Ala Gly Leu Lys Lys
    1235            1240            1245

Lys Lys Ser Val Thr Val Leu Asp Val Gly Asp Ala Tyr Phe Ser
    1250            1255            1260

Val Pro Leu Asp Glu Ser Phe Arg Lys Tyr Thr Ala Phe Thr Ile
    1265            1270            1275

Pro Ser Thr Asn Asn Glu Thr Pro Gly Val Arg Tyr Gln Tyr Asn
    1280            1285            1290

Val Leu Pro Gln Gly Trp Lys Gly Ser Pro Ile Phe Gln Ser Ser
    1295            1300            1305

Met Thr Lys Ile Leu Glu Pro Phe Arg Ser Lys Asn Pro Asp Ile
    1310            1315            1320

Val Ile Tyr Gln Tyr Met Asp Asp Leu Tyr Val Gly Ser Asp Leu
    1325            1330            1335

Glu Ile Gly Gln His Arg Thr Lys Ile Glu Glu Leu Arg Ala His
    1340            1345            1350

Leu Leu Ser Trp Gly Phe Ile Thr Pro Asp Lys Lys His Gln Lys
    1355            1360            1365

Glu Pro Pro Phe Leu Trp Met Gly Tyr Glu Leu His Pro Asp Lys
    1370            1375            1380

Trp Thr Val Gln Pro Ile Glu Leu Pro Glu Lys Asp Ser Trp Thr
    1385            1390            1395

Val Asn Asp Ile Gln Lys Leu Val Gly Lys Leu Asn Trp Ala Ser
    1400            1405            1410

Gln Ile Tyr Ala Cys Thr Pro Tyr Asp Ile Asn Gln Met Leu Arg
    1415            1420            1425

Gly Pro Gly Arg Ala Phe Val Thr Ile Pro Asn Pro Leu Leu Gly
    1430            1435            1440

Leu Asp
    1445
```

<210> SEQ ID NO 33
<211> LENGTH: 4349
<212> TYPE: DNA
<213> ORGANISM: Artificial Sequence
<220> FEATURE:
<223> OTHER INFORMATION: Description of Artificial Sequence: Synthetic chimeric polynucleotide sequence

<400> SEQUENCE: 33

| | | | | | |
|---|---|---|---|---|---|
| cccgccgcca | ccatgcccat | cgtgcagaac | gcccagggcc | agatgcacca | ggccctgtcc | 60 |
| ccccgcaccc | tgaacgccct | ggtgaaggtg | atcgaggaga | aggccttctc | ccccgaggtg | 120 |
| atccccatgt | tctccgccct | gtccgagggc | gccaccccc | aggacctgaa | catgatgctg | 180 |
| aacatcgtgg | gcggccacca | ggccgccatg | cagatgctga | aggacaccat | caacgaggag | 240 |
| gccgccgagt | gggaccgcct | gcaccccgtg | cacgccggcc | ccatcccccc | cggccagatg | 300 |
| cgcgagcccc | gcggatccga | catcgccggc | accacctcca | ccctgcagga | gcagatcggc | 360 |
| tggatgacct | ccaaccccc | catccccgtg | ggcgacatct | acaagcgctg | gatcatcctg | 420 |
| ggcctgaaca | agatcgtgcg | catgtactcc | cccgtgtcca | tcctggacat | ccgccagggc | 480 |
| cccaaggagc | ccttccgcga | ctacgtggac | cgcttcttca | agaccctgcg | cgccgagcag | 540 |
| gccacccagg | aggtgaagaa | ctggatgacc | gagaccctgc | tggtgcagaa | cgccaacccc | 600 |
| gactgcaagt | ccatcctgcg | cgccctgggc | cccggcgcca | ccctggagga | gatgatgacc | 660 |
| gcctgccagg | gcgtgggcgg | ccccggccac | aaggcccgcg | tgctgggtac | cggcgcccgc | 720 |
| gcctccgtgc | tgtccggcgg | caagctggac | gcctgggaga | gatccgcct | gcgccccggc | 780 |
| ggcaagaaga | agtaccgcct | gaagcacctg | gtgtgggcct | cccgcgagct | ggagcgcttc | 840 |
| gccctgaacc | cctccctgct | ggagaccgcc | gagggctgcc | agcagatcat | ggagcagctg | 900 |
| cagtccgccc | tgaagacctc | cgaggagctg | aagtccctgt | caacaccgt | ggccaccctg | 960 |
| tactgcgtgc | accagcgcat | cgacgtgaag | gacaccaagg | aggccctgga | caagatcgag | 1020 |
| gagatccaga | acaagtccaa | gcagaagacc | cagcaggccg | ccgccgacac | ccagtcctcc | 1080 |
| tccaaggtgt | cccagaacta | cgccctgaag | caccgcgcct | acgagctgga | attcggcatc | 1140 |
| aaggtgaagc | agctgtgcaa | gctgctgcgc | ggcgccaagg | ccctgaccga | catcgtgacc | 1200 |
| ctgaccgagg | aggccgagct | ggagctggcc | gagaaccgcg | agatcctgaa | ggaccccgtg | 1260 |
| cacggcgtgt | actacgaccc | ctccaaggac | ctgatcgccg | agatccagaa | gcagggccag | 1320 |
| gaccagtgga | cctaccaaat | ctaccaggag | cccttcaaga | acctgaagac | cggcaagtac | 1380 |
| gcccgcaagc | gctccgccca | gaccaacgac | gtgaagcagc | tggccgaggt | ggtgcagaag | 1440 |
| gtggtgatgg | agtccatcgt | gatctgggc | aagaccccca | agttccgcct | gcccatccag | 1500 |
| aaggagacct | gggagacctg | gtggatgac | tactggcagg | ccacctggat | tcccgagtgg | 1560 |
| gagttcgtga | cacccccacc | cctggtgaag | ctgtggtatc | agctggagaa | ggaccccatc | 1620 |
| gccggcgccg | agaccttcta | cgtggacggc | gccgccaacc | gcgagaccaa | gctgggcaag | 1680 |
| gccggctacg | tgaccgaccg | gggccgccag | aaggtggtgt | ccctgaccga | gaccaccaac | 1740 |
| cagaagaccg | agctgcacgt | catccacctg | gccctgcagg | actccggctc | cgaggtgaac | 1800 |
| atcgtgaccg | actcccagta | cgccctgggc | atcatccagg | cccagcccga | cagatctgac | 1860 |
| cccgtggacc | ccaacctgga | gcctggaac | caccccggct | cccagcccac | cacccccggc | 1920 |
| tccaagtgct | actgcaaggt | gtgctgctac | cactgccccg | tgtgcttcct | gaacaagggc | 1980 |
| ctgggcatct | cctacggccg | caagaagcgc | gccagcgcc | gcggcacccc | ccagtccaac | 2040 |
| aaggaccacc | agaaccccat | ccccaagcag | cccatccccc | agacccaggg | catctccacc | 2100 |

```
ggccccaagg agtccaagaa gaaggtggag tccaagaccg agaccgaccc cgaggacgcc    2160
ggccgctccg gcaactccga cgaggagctg ctgaaggcca tccgcatcat caagatcctg    2220
taccagtcca acccctaccc caagcccaag ggctcccgcc aggcccgcaa gaaccgccgc    2280
cgccgctggc gcgccggcca cgccagatc gactccctgt ccgagcgcat cctgtccacc    2340
tgcctgggcc gccccgccga gcccgtgccc ctgcagctgc ccccctgga gctggactgc    2400 tccgaggact gcggcacctc cggcacccag cagtcccagg gcgccgagac cggcgtgggc    2460
cgcccccagg tgtccgtgga gtcctccgcc gtgctgggct ccggcaccaa ggagggtacc    2520 gtgcgcccc aggtgcccct cgccccatg acctacaagg ccgccttcga cctgtccttc    2580
tttctgaagg agaagggcgg cctggacggc ctgatctact ccaagaagcg ccaggagatc    2640
ctggacctgt gggtgtacca cacccagggc tacttccccg actggcagaa ctacacccc    2700 ggccccggca tccgctaccc cctgaccttc ggctggtgct tcaagctggt gcccgtggac    2760
cccgacgagg tggaggaggc caccggcggc gagaacaact ccctgctgca ccccatctgc    2820
cagcacggca tggacgacga ggagaaggag accctgcgct ggaagttcga ctcctccctg    2880
gccctgaagc accgcgcccg cgaactccac cccgagtcct acaaggactg cccccagatc    2940
accctgtggc agcgccccct ggtgaccaag atcggcggcc agaagacgcg tggcggcaag    3000
tggtccaagt cctccatcgt gggctggccc gaggtgcgcg agcgcatccg ccagaccccc    3060
accgccgccc gcgagcgcac ccgccaggcc cccaccgccg ccaaggtggg cgccgtgtcc    3120
caggacctgg acaagcacgg cgccgtgtcc tccaacgtga ccaccccctc ctgccgcctgg    3180 ctggaggccc aggaagagga agaggtgggc ttccccgagc tcctggacac cggcgccgac    3240
gacaccgtgc tggaggacat caacctgccc ggcaagtgga agcccaagat gatcggcggc    3300
atcggcggct tgatcaaggt gaagcagtac gaccagatcc tgatcgaaat ctgcggcaag    3360
aaggccatcg gcaccgtgct ggtgggcccc accccgtga acatcatcgg ccgcaacatg    3420
ctgacccaga tcgctgcac cctgaacttc cccatctccc ccatcgagac cgtgcccgtg    3480
aagctgaagc ccggcatgga cggccccaag gtgaagcagt ggcccctgac cgaggagaag    3540
atcaaggccc tgaccgaaat ctgcgccgac atggagaagg agggcaagat cagtaagatc    3600
ggccccgaga acccctacaa caccccatc ttcgccatca gaagaagca gtccaccaag    3660 tggcgcaagc tggtggactt ccgcgagctg aacaagcgca cccaggactt ctgggaggtg    3720
cagctgggca tccccaccc cgccggcctg aagaagaaaa agtccgtgac cgtgctggac    3780
gtgggcgacg cctacttctc cgtgcccctg gacgagtcct tccgcaagta caccgccttc    3840
accatcccct ccaccaacaa cgagaccccc ggcgtgcgct accagtacaa cgtgctgccc    3900
cagggctgga agggatcccc catcttccag tcctccatga ccaagatcct ggagccttc    3960 cgctccaaga accccgacat cgtgatctac cagtacatgg acgacctgta cgtgggctcc    4020
gacctggaga tcgccagca ccgcaccaag atcgaggagc tgcgcgccca cctgctgtcc    4080
tggggcttca tcaccccga caagaagcac cagaaggagc ccccttcct gtggatgggc    4140 tacgagctgc accccgacaa gtggaccgtg cagcccatcg agctgcccga aaggactcc    4200 tggaccgtga cgacatcca gaagctggtg ggcaagctga actgggcctc ccaaatctac    4260
gcctgcaccc cctacgacat caaccagatg ctgcgcggcc ccggccgcgc cttcgtgacc    4320
atccccaacc ccctgctggg cctggacta                                     4349
```

CHIMERIC HUMAN IMMUNODEFICIENCY VIRUS (HIV) IMMUNOGENS COMPRISING GAG P24-P17 FUSED TO MULTIPLE CYTOTOXIC T LYMPHOCYTE (CTL) EPITOPES

FIELD OF THE INVENTION

This invention relates to an immunogen designed to elicit an anti-HIV immune response in a human subject (especially a cell-mediated response), a nucleic acid molecule encoding the immunogen, compositions comprising the immunogen and/or the nucleic acid molecule, and to a method of inducing an anti-HIV immune response (especially a cell-mediated response) in a human subject.

BACKGROUND OF THE INVENTION

Development of effective human immunodeficiency virus (HIV) vaccines is one of the primary goals of current acquired immunodeficiency syndrome (AIDS) research. Despite progress in prevention and powerful drug combinations to treat HIV infection, an estimated 16,000 people become infected every day. Over 90% of new infections occur in developing countries for which the recent medical advances are not immediately applicable or affordable. The best hope for these countries is the development of an effective, accessible HIV vaccine. There is now growing optimism among scientists that an AIDS vaccine may be possible (Mc-Michael & Hanke 1999 Nat. Med. 5, 612-614; Gold 1999 IAVI Report 4, pp 1-2, 8-9, 15-16 & 18).

An ideal prophylactic vaccine should induce sterilizing immunity, so that after exposure, the virus would never be detected in the body. However, this is probably an unrealistic objective. Rather, an attainable goal may be a vaccine-induced immunity that results in a limited and transient virus replication, after which the virus becomes undetectable, there are no signs of disease and no transmission to other individuals. Alternatively, a potentially successful vaccine may induce immune responses that at least hold the virus in check at levels so low, that both progression to AIDS and transmission are entirely or substantially prevented.

To induce sterilizing immunity, a prophylactic vaccine may need to elicit both humoral and cell-mediated immune responses. Since HIV was isolated and sequenced, there has been a considerable effort to develop envelope-based vaccines inducing neutralizing antibodies (nAb). However, this has proved to be exceedingly difficult (Heilman & Baltimore 1998 Nat. Med. 4 (4 Suppl.) 532-534). Although some success was reported in inducing nAb against laboratory HIV strains (Berman et al, 1990 Nature 345, 622-625; Fultz et al, 1992 Science 256, 1687-1690), it has been extremely difficult to neutralize primary isolates (Trkola et al, 1998 J. Virol. 72, 1876-1885; Haynes 1996 Lancet 34, 933-937). An explanation for the first 15 years of relative failure has been provided by the crystal structure of the core gp 120, which revealed multiple mechanisms by which HIV prevents efficient induction of nAb (Wyatt et al, 1998 Nature 393, 705-711; Kwong et al, 1998 Nature 393, 638-659). As a result of these difficulties, the emphasis of many vaccine designers has shifted to the induction of cell-mediated immune responses, which are mediated (predominantly) by cytotoxic T lymphocytes.

Cytotoxic T lymphocytes (CTL) are usually CD8$^+$ cells and participate in an organism's defence in at least two different ways: they kill virus-infected cells; and they secrete a variety of cytokines and chemokines that directly or indirectly contribute to the suppression of virus replication. CTL-mediated protection after vaccination may depend on the levels of CTL present in the circulation and, perhaps, specifically for proteins expressed early (regulatory proteins) rather than late (structural proteins) in the replication cycle.

The induction and maintenance of CD8$^+$ T cell responses require "help" provided by CD4$^+$ T lymphocytes (helper T cells). In some HIV-infected individuals, high levels of HIV-specific helper response have been detected.

Identification of methods for induction of strong CD8$^+$ T cell responses would provide tools for studying their role(s) in shaping the course of HIV infection and may stimulate progress towards an effective HIV vaccine. Previously, a prototype HIV vaccine was constructed as a string of partially overlapping epitopes recognised by murine, macaque and human CTL, which was delivered by vaccine vehicles that were safe and acceptable for use in humans, a DNA vector and modified vaccinia virus Ankara (MVA) vector (Hanke et al, 1998 Vaccine 16, 426-435; Hanke et al, 1998 J. Gen. Virol. 79, 83-90). In mice, the most potent protocol for induction of CTL was found to be DNA priming followed by MVA boosting (Hanke et al, 1998 Vaccine 16, 439-445; Schneider et al, 1998 Nat. Med. 4, 397-402) that is, priming mice with nucleic acid encoding the relevant polypeptide, followed by boosting the mice by inoculation with a modified vaccinia virus Ankara ("MVA") vector expressing the relevant epitopes.

WO 98/56919 discloses a "prime-boost" vaccination strategy, involving (i) priming with a composition comprising a source of one or more T cell epitopes of a target antigen, together with a pharmaceutically acceptable carrier, and (ii) boosting with a composition comprising a source of one or more T cell epitopes of the target antigen, including at least one T cell epitope that is the same as a T cell epitope of the priming composition.

The present invention aims, inter alia, to provide immunogens which may be useful in eliciting an HIV-specific response in humans. All documents and publications mentioned in this specification are incorporated herein by reference.

SUMMARY OF THE INVENTION

In a first aspect the invention provides an immunogen in sterile form suitable for administration to a human subject, the immunogen comprising: at least a portion of the gag protein of HIV, said gag protein being from an HIV clade or having a consensus sequence for one or more HIV clades, and comprising at least parts of p17 and p24; and a synthetic polypeptide comprising a plurality of amino acid sequences, each sequence comprising a human CTL epitope of an HIV protein, and wherein a plurality of HIV proteins are represented in the synthetic polypeptide, said CTL epitopes being selected to stimulate an immune response to one or more HIV clades of interest.

For present purposes "sterile" refers to the general absence of viruses, bacteria, fungi, yeasts, chlamydia, mycoplasma, and spores of any of the foregoing (especially microbes pathogenic in humans). However, the immunogen may comprise one or more specific known microbial (e.g. viral or bacterial) vectors which serve to express the gag protein and/or synthetic polypeptide in a human subject. Such vectors are well known to those skilled in the art and include, for example, viruses such as adenoviruses and pox viruses which are inherently non-pathogenic in humans or have been subjected to genetic manipulation or other modification to render them non-pathogenic in humans. Particularly preferred is vaccinia virus, especially modified vaccinia virus Ankara (MVA). Other specific preferred viral vectors include Semliki Forest Virus (SFV) and Sindbis virus (see Smerdon & Liljeström 2000, Gene Ther. Regul. 1, 1-31). Suitable bacterial vectors include BCG, and attenuated strains of Salmonella Spp. (especially "double aro" mutants of Salmonella which are being developed as vaccines for diarrhoeal diseases), and Shigella (see Shata et al, 2000 Mol. Med. Today 6, 66-71).

Other expression systems, which may be useful for producing the immunogen include a tobacco mosaic virus (TMV) expression vector (Palmer et al, 1999 Arch. Virol. 144, 1345-60) and NS1 tubules of bluetongue virus (Adler et al, 1998 Med. Microbiol. Immunol. (Berl.) 187, 91-96).

The term "synthetic" as used herein, is intended to refer to a polypeptide which is not, in its entirety, present in any naturally-occurring HIV isolate. The term "synthetic" is not intended to indicate that the polypeptide is necessarily synthesised by conventional chemical techniques of solid phase peptide synthesis. Whilst this represents one possibility, it is generally to be preferred that the polypeptide is synthesised by transcription and/or translation from an appropriate nucleic acid molecule encoding the synthetic polypeptide. Such methods of synthesis are well known to those skilled in the art and form no part of the invention.

It is preferred that the gag protein (or portion thereof) and the synthetic polypeptide are joined in some way on a single entity. For example, a viral vector may express both the gag protein and the synthetic polypeptide as separate components of the immunogen. Alternatively, both components of the immunogen may be covalently coupled or conjugated to each other or to a common carrier entity (such as a liposome, ISCOM or molecule). In preferred embodiments, both the gag protein and the synthetic polypeptide components of the immunogen are present in a single polypeptide or fusion protein. In such a fusion protein, the gag protein and synthetic polypeptide may be essentially the only components present. Alternatively the fusion protein may comprise other components which may correspond to other HIV antigens (or portions thereof), or may be derived from other sources. Thus, in some embodiments, the polypeptide will comprise a portion of the gag protein substantially adjacent to the synthetic polypeptide (i.e. with fewer than 10 intervening amino acid residues). In other embodiments, the portion of the gag protein and the synthetic polypeptide may be separated by one or more intervening components (i.e. with 10 or more intervening amino acid residues), which will typically comprise one or more further HIV antigens.

It is also generally preferred that the immunogen does not contain the entire gag protein amino acid sequence. Typically between 55 and 95% of the gag protein will be present, preferably between 65 and 85%, most preferably about 75%.

The wild type HIV gag protein is known to consist of three portions termed p17, p24 and p15. These are synthesised in infected cells as a single polyprotein, with p17 at the N terminus. Normally, in HIV-infected cells, the N terminus of p17 is myristylated.

It is desirable that the gag portion of the immunogen will comprise at least part of p17 and p24, but it is generally preferred that the p17 component will be modified in some way to prevent myristylation. Conveniently this can be accomplished by reversing the order of the p17 and p24 components in the immunogen, such that p17 is no longer at a free N terminus and cannot therefore be myrisylated. The inventors believe that this may improve the efficiency of presentation of peptides, derived from the immunogen, to a subject's immune system.

The gag protein component of the immunogen will generally comprise at least one T-helper cell, HLA Class II-restricted, peptide epitope and preferably comprise a plurality of such epitopes (preferably such that a number of different HLA Class II-restricted alleles are represented in the gag component). The gag protein component will also typically comprise one or more CTL HLA Class I-restricted peptide epitopes.

The synthetic polypeptide component of the immunogen will conveniently take the form of a string of CTL epitopes, each represented by, or contained within, a respective sequence of about 8-12 amino acids. Desirably at least some (preferably most) of the epitopes will be partially overlapping (such that one or more amino acids of one epitope will also be contained within the sequence of an adjoining epitope). Some "non-epitopic" amino acid sequence may be present between neighbouring epitopes, but this is generally to be avoided.

Non-epitopic amino acid sequence between neighbouring epitopes is preferably less than 20 amino acid residues, more preferably less than 10 residues, and most preferably 1-5 amino acid residues. It will be apparent that such non-epitopic amino acid sequence may comprise linkers, spacers and the like which optimise the expression levels of the synthetic polypeptide or optimise its immunogenicity.

Thus in one extreme embodiment, all of the human CTL epitopes in the synthetic polypeptide may be overlapping and, at the other extreme, every epitope may be separated from its neighbours by at least some non-epitopic amino acid sequence. It is generally to be preferred that at least 50% of the human CTL epitopes are overlapping.

In addition to overlapping epitopes, the synthetic polypeptide may comprise at least some "adjacent epitopes". The term adjacent epitopes refers to epitopes which are not overlapping but which are not separated by any intervening non-epitopic amino acid sequence.

Thus in preferred embodiments the synthetic polypeptide comprises a mosaic pieced together from small (typically about 10-20 amino acid residue) fragments of different HIV proteins, which fragments will typically comprise one, two or three known adjacent and/or overlapping human CTL epitopes. Where a plurality of fragments are present in the synthetic polypeptide from the same HIV protein, the fragments will typically have been selected from discontinuous portions of the protein, so that it is unlikely that the synthetic polypeptide comprises a sequence corresponding to more than 20-25 consecutive amino acid residues of a particular HIV protein. Generally the synthetic polypeptide is designed so as essentially to omit those portions of HIV proteins not known to contain any human CTL epitopes.

A plurality of different HIV proteins will preferably be represented in the synthetic polypeptide. The synthetic polypeptide may contain epitopes present in any HIV antigen, but preferably will comprise at least one epitope present in one or more of the following: p24; pol; gp41; gp120; and nef. In one preferred embodiment, the synthetic polypeptide comprises at least one CTL epitope present in each of the aforementioned HIV proteins. The synthetic polypeptide may additionally comprise at least one CTL epitope present in each of the following HIV proteins: vpr, vpu, vif (and especially) tat and rev.

It will be understood that the term "human CTL epitope" as used herein refers not to the origin of the protein from which the epitope derives, but indicates that the epitope is recognized and responded to by the CTL of at least a portion of the human population. Typically a human CTL epitope will be recognized by at least 0.01%, preferably 0.1%, and more preferably at least 1% of the world's human population.

In one particular embodiment, the immunogen specifically excludes any epitope from the env protein generally recognised by the human immune system. Most presently-used diagnostic tests are based on detection of an HIV env-specific immune response, so by excluding env components from the immunogen it is possible to distinguish between immune responses rising from infection with the virus and inoculation with the immunogen.

In one embodiment, the CTL epitopes present in the synthetic polypeptide are selected such that an immune response to HIV clade A will be generated. Preferably however, the synthetic polypeptide is large enough, and the CTL epitopes appropriately selected, such that an immune response which is cross-reactive against different HIV clades will be stimulated. This can conveniently be achieved by including one or more CTL epitopes which are conserved among different HIV clades. Several such epitopes are known to those skilled in the art (see Table 1 below).

In a preferred embodiment, the immunogen comprises at least one epitope (conveniently a CTL epitope) which is recognized by one or more laboratory test mammals, (e.g. mouse and/or monkey). Such an epitope can readily be incorporated within the synthetic polypeptide. Inclusion of an epitope of this sort allows for the quality, reproducibility and/or stability of different batches of the immogen to be assayed in a potency assay using the laboratory test mammal (such as a mouse or macaque monkey). Examples of such epitopes include the amino acid sequence ACTPYDINQML (Seq. ID No. 1; containing a dominant epitope derived from simian immunodeficiency virus, SIV, gag p27, recognised by rhesus macaque monkey CTLs) and RGPGRAFVTI (Seq. ID No. 2; an H-2$D^d$-restricted CTL mouse epitope derived from HIV env protein).

A list of some 23 human CTL epitopes suitable for inclusion in the synthetic polypeptide is shown in Table 1. The list is not exhaustive. A preferred immunogen will comprise at least 10 of such human CTL epitopes, more preferably at least 15, most preferably at least 20. In a particular embodiment each of the 23 human CTL epitopes listed in Table 1 will be represented in the synthetic polypeptide, optionally together with the macaque and murine epitopes also listed in Table 1.

Desirably the immunogen may additionally comprise a small tag or marker. Such a tag or marker should be as small as possible, in order to minimise the amount of extraneous material present in the immunogen. A convenient tag or marker allows for detection of expression and/or quantification of the amount of immunogen. Suitable tags include epitopes recognized by the monoclonal antibody Pk (Hanke et al, 1992 J. Gen. Virol. 73, 653-660).

The immunogen of the invention will conveniently be mixed with other substances in order to provide a vaccine composition. For example, a vaccine composition may additionally comprise one or more of the following: an adjuvant (e.g. alum), liposome, or immunostimulatory complex (ISCOM). A vaccine will also generally comprise a sterile diluent, excipient or carrier, such as a physiologically acceptable liquid (e.g. saline or phosphate-buffered saline solutions). The vaccine may be presented as a liquid or, more preferably, as a freeze-dried solid, which is suspended or dissolved in a physiologically acceptable liquid prior to administration.

Methods of administering the immunogen to a human subject will be apparent to those skilled in the art. Such methods include, in particular, intramuscular injection, subcutaneous injection, or delivery through the skin by needleless injection device. Alternatively, vaccines (especially those comprising bacterial vectors e.g. attenuated *Salmonella* or *Shigella* spp.) may be given orally, intranasally or by any other suitable route. A suitable dose of immunogen may typically be from 1 to 500 mg, typically from 10 to 100 mg, depending on the size of the immunogen, the body mass of the recipient etc. A suitable dose can, if necessary, be ascertained by routine trial-and-error with different groups of subjects being given different doses of immunogen, and the immune response of the subjects to the immunogen assayed in order to determine optimum dose size. The immune response of the subjects can be assayed by conventional immunological techniques (e.g. chromium release assay, using peripheral blood lymphocytes obtained from subjects' blood samples, acting on peptide-pulsed or virus-infected chromium-labelled target cells).

In a second aspect, the invention provides a nucleic acid molecule encoding a fusion protein, the fusion protein comprising an immunogen in accordance with the first aspect of the invention defined above.

The nucleic acid molecule is preferably in isolated, sterile form, suitable for administration to a human subject. The nucleic acid molecule is preferably "humanized" i.e. employs codons to code particular amino acids, which codons are frequently used in highly expressed human genes (Andre et al, 1998 J. Virol. 72, 1497-1503), instead of those codons used by HIV.

Desirably the nucleic acid molecule is contained within a vector, the sequence encoding the immunogen being operably linked to a promoter sequence active in human cells. Conveniently the promoter is a strong viral promoter such as the promoter from human cytomegalovirus (CMV). The vector will preferably also comprise an enhancer and polyadenylation signals, which are functional in human cells. Ideally, for maximum safety, the vector should not contain any origin of replication functional in human cells, to prevent undesirable replication of the vector.

The vector may be administered to the subject in isolation, as essentially 'naked' nucleic acid (preferably DNA), or else may be packaged within a delivery means, such as a virus, bacterium, liposome, or gold-coated particles and the like. One suitable delivery means is the modified vaccinia virus Ankara (MVA): the immunogen gene or open reading frame (ORF) may be inserted into MVA, for example, at the thymidine kinase locus.

It will be appreciated by those skilled in the art that a vector may comprise a nucleic acid encoding an immunogen (the nucleic acid therefore being in accordance with the second aspect of the invention), and that the vector may also possess, at its surface or internally, the polypeptide immunogen in accordance with the first aspect of the invention.

Whether administered as naked nucleic acid, or packaged within a delivery means, at least some of the administered nucleic acid enters the cells of the subject and is transcribed (if necessary) and translated, resulting in the in situ synthesis of the immunogen in the subject, who then develops an immune response to the immunogen.

As with the immunogen preparation per se, a nucleic acid encoding the immunogen may be administered to a human subject by any of a number of known routes e.g. subcutaneous or intramuscular injection, oral delivery, or delivery through the skin by means of needleless injector. Particular examples of administration by needleless injection device are disclosed in WO 97/34652 and WO 97/48485. A suitable dose of nucleic acid may be from 10 μg to 10 mg, typically from 100 μg to 1 mg, depending on the size of nucleic acid molecule, route of administration, body mass of the recipient etc. Again, routine trial and error (with the benefit of the present teaching) will enable those skilled in the art to determine an optimum dose of the nucleic acid.

Successful delivery of DNA to animal tissue has been achieved by cationic liposomes [Watanabe et al., Mol. Reprod. Dev. 38:268-274 (1994); Sharkey et al, WO 96/20013], direct injection of naked DNA into animal muscle tissue [Robinson et al., Vacc. 11:957-960 (1993); Hoffman et al., Vacc. 12:1529-1533; (1994); Xiang et al., Virol. 199:132-140 (1994); Webster et al., Vacc. 12:1495-1498 (1994); Davis et al., Vacc. 12:1503-1509 (1994); and Davis et al., Hum. Molec. Gen. 2:1847-1851 (1993)], and embryos [Naito et al., Mol. Reprod. Dev. 39:153-161 (1994); and Burdon et al., Mol. Reprod. Dev. 33:436-442 (1992)], or intradermal injection of DNA using "gene gun" technology [Johnston et al., Meth. Cell Biol. 43:353-365 (1994)].

For DNA-based vaccination, delivery by injection of naked plasmid DNA has shown potential in mouse models for inducing both humoral and cellular immune responses. However, in larger animals, using DNA delivery for vaccination has been hampered by requiring large amounts of DNA or inducing persistent expression of an antigen with the potential for developing tolerance to the antigen. Berglund reported a strategy for inducing or enhancing an immune response by injecting mice with plasmid DNA containing an alphavirus DNA expression vector having a recombinant Semliki Forest Virus (SFV) replicon in a eukaryotic expression cassette [Berglund et al., Nature Biotechnol. 16:562-565 (1998)]. The eukaryotic expression cassette controlled expression of the primary nuclear transcription of the SFV replicon. This SFV replicon transcript, encoding the heterologous antigen, was transported to the cytoplasm and amplified by the self-encoded SFV replicase complex. The amplified RNA replicon lead to high level production of an mRNA encoding the heterologous antigen. Similar results were described by Polo and his group [Polo et al., Nature Biotechnol. 16:517-518 (1998); Hariharan et al., J. Virol. 72:950-958 (1998)]. Both groups found strong immune responses could be induced using small amounts of input plasmid DNA.

Alternatively, a method to deliver DNA to animals that overcomes the disadvantages of conventional delivery methods is by administering attenuated, invasive bacteria containing a bacterial DNA vector having a eukaryotic expression cassette encoding the gene to be expressed. For example, U.S. Pat. No. 5,877,159 to Powell et al., describes live bacteria that can invade animal cells without establishing a productive infection or causing disease to thereby introduce a eukaryotic expression cassette encoding an antigen capable of being expressed by the animal cells.

In a third aspect the invention provides a method of stimulating an anti-HIV immune response in a human subject, the method comprising preparing an immunogen in accordance with the first aspect of the invention, or a nucleic acid molecule in accordance with the second aspect of the invention; and administering said immunogen or nucleic acid molecule to the subject.

Conveniently, the method comprises the administering both the immunogen and the nucleic acid molecule. In particular, the method preferably comprises one or more administrations of the nucleic acid molecule ("priming") followed at a suitable interval (e.g. 1 week to 4 months) by one or more administrations of the immunogen ("boosting"). Boosting may be performed, for example, by administering a replication-competent (e.g. attenuated virus or bacterium) or non-replicating vector comprising the immunogen and/or a nucleic acid molecule encoding the immunogen. Preferably boosting is achieved by administering the immunogen as part of an MVA viral particle, which particle may advantageously comprise a nucleic acid encoding the immunogen.

In a preferred embodiments, performance of the method will result in the generation in the subject of a protective immune response such that, should the subject subsequently be exposed to HIV infection, the subject will not go on to develop the symptoms of AIDS associated with HIV infection.

In a fourth aspect the invention provides for use of an immunogen in accordance with the first aspect of the invention and/or a nucleic acid in accordance with the second aspect of the invention in the preparation of a medicament to prevent or treat HIV infection in a human subject.

In a fifth aspect, the invention provides a nucleic acid sequence encoding the amino acid sequence shown in FIG. 8A. Conveniently the nucleic acid comprises or essentially consists of the nucleotide sequence shown in FIG. 8B.

In a sixth aspect, the invention provides a polypeptide comprising the amino acid sequence shown in FIG. 8A.

The nucleic acid of the fifth aspect and/or the polypeptide of the sixth aspect may be used in immunogen/vaccine compositions as described in relation to the other aspects of the invention, and such immunogens and vaccines are accordingly considered within the scope of the invention, and may comprise vectors etc (especially MVA) as aforesaid. The invention further provides, in a seventh aspect, a method of stimulating an anti-HIV immune response in a human subject, the method comprising administering to the subject a nucleic acid in accordance with the fifth aspect of the invention and/or a polypeptide in accordance with the sixth aspect of the invention. Finally, the invention provides for use of a nucleic acid in accordance with the fifth aspect of the invention and/or a polypeptide in accordance with the sixth aspect of the invention in the preparation of a medicament to prevent or treat HIV infection in a human subject.

The invention will now be further described by way of illustrative example and with reference to the accompanying drawings, wherein:

FIG. 1A is a schematic representation of immunogens, HIV A, HIVTA and HIVAeT in accordance with the invention; and an immunogen PPA;

FIG. 1B shows the amino acid sequence of the HIVA immunogen (Seq. ID No. 26);

FIG. 2A shows the nucleotide sequence (Seq. ID No. 27) of a nucleic acid (termed "HIVA gene") encoding the HIV A immunogen;

Figure 5A:
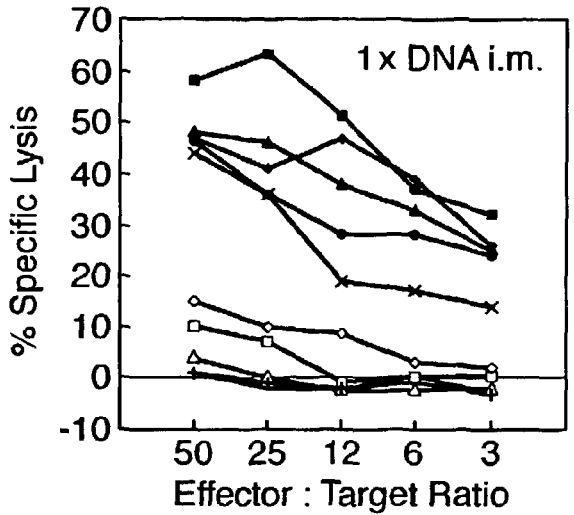

FIGS. 5A, B & C are graphs showing the results of chromium release assays using a splenocytes obtained from mice inoculated with a DNA molecule or an immunogen in accordance with the invention;

FIG. 6A shows the amino acid sequence of the HIV TA immunogen (Seq. ID No. 28);

FIG. 6B shows the nucleotide sequence (Seq. ID No. 29) of a nucleic acid molecule encoding the HIV TA immunogen;

FIG. 7A shows the amino acid sequence (Seq. ID No. 30) of the tat polypeptide present in the HIVAeT immunogen;

FIG. 7B shows the nucleotide sequence (Seq. ID No. 31) of a nucleic acid molecule encoding the HIVAeT immunogen;

FIG. 8A shows the amino acid sequence (Seq. ID No. 32) of the PPA immunogen which is in accordance with the sixth aspect of the invention; and FIG. 8B shows the nucleotide sequence (Seq. ID No. 33) of a nucleic acid molecule (in accordance with the fifth aspect of the invention) encoding the PPA immunogen.

EXAMPLES

Example 1

This example relates to an immunogen for use in a vaccine focusing on the induction of cellular immune responses mediated by a concerted action of CD4+ helper and CD8+ effector T lymphocytes. The immunogen, designated HIVA (Hanke & McMichael Nat. Med. 6, 951-955), was designed for a phase III efficacy trial in Nairobi, Kenya. FIG. 1A is a schematic representation of several immunogens, including HIVA. HIVA is derived from the sequences of HIV-1 clade A, the predominant HIV clade in Nairobi and consists of about 73% of the gag protein fused to a string of 25 partially overlapping CTL epitopes. The gag domain of HIVA contains p24 and p17 in an order reversed to the viral gag p17-p24-p15 polyprotein. This rearrangement prevents myristylation of the N-terminus of p17, which could direct the recombinant protein to the cell membrane, thus preventing efficient degradation into peptides necessary for the major histocompatibility complex (MHC) class I presentation.

FIG. 1B shows the amino acid sequence (Seq. ID No. 26) of the HIVA immunogen. Amino acids corresponding to the restriction endonuclease sites used to assemble the gene are shown in bold (GS-corresponds to Bam HI, GT corresponds to KpnI and EF correspnds to EcoRI).

The amino acid sequence of the gag domain was derived from the protein database consensus sequence of HIV-1 clade A (Korber et al, "Human retroviruses and AIDS: a compilation and analysis of nucleic acid and amino acid sequences" 1997). In the absence of available Kenyan strain sequences, regions without a strong amino acid lade A preference were biased towards Ugandan isolates. The HIV-1 gag protein contained not only important MHC class I-, but also class II-restricted epitopes which stimulate CD4+ T helper cells.

The C-terminus of the HIVA protein was designed as a multi-CTL epitope synthetic polypeptide. The CTL epitopes included in HIVA were recognised by CTL in patients infected with HIV-1 clade A stains circulating in Kenya, were 8- to 10-amino acids long, and originate from the gag, pol, nef or env proteins Rowland-Jones et al, 1998 J. Clin. Invest. 102, 1758-1765; Dorrell et al, 1999 J. Virol. 73, 1708-1714). Many of these epitopes are immunodominant and relatively conserved among other HIV-1 clades (Table 1) (and therefore should be able to elicit an immune response which cross-reacts with HIV viruses of clades other than clade A). They are presented by seventeen different HLA alleles, which include both frequent African alleles as well as alleles common in most ethnic populations. It has been estimated that optimally selected epitopes presented by the nine commonest HLA alleles could cover the general population irrespective of ethnic descent (Sydney et al, 1996 Immunol. Today 17, 261-266). Thus, given that majority of HIV-infected donors make good CTL responses to gag p17/p24, each vaccinee should have the potential to respond to at least two or three CTL epitopes present in the HIVA protein.

The HIVA synthetic polypeptide also comprised SIV gag and HIV env epitopes recognised by macaque and murine CTL, respectively, so that the quality, reproducibility and stability of the clinical batches could easily be assessed in a mouse (or macaque if necessary) potency assay. A monoclonal antibody epitope Pk (Hanke et al, 1992 J. Gen. Virol. 73, 653-660) was added to the C-terminus of HIVA for easy detection of the full-size protein and estimation of the level of expression. There is no reason to believe that the three non-HLA epitopes represent a health hazard for the vaccinated individuals.

TABLE 1

CD8+ cell epitopes included in the HIVA synthetic polypeptide polyepitope region.

| Epitope[a] | SEQ ID NO: | MHC class I restriction | Origin | HIV clade[b] |
|---|---|---|---|---|
| ALKHRAYEL | 3 | HLA-A*0201 | nef | a |
| PPIPVGEIY | 4 | HLA-B35 | p24 | a/B/c/D/F/G |
| GEIYKRWII | 5 | HLA-B8 | p24 | a/B/c/D/F/G |
| KRWIILGLNK | 6 | HLA-B*2705 | p24 | A/B/C/D/F/G/H |
| FRDYVDRFYK | 7 | HLA-B18 | p24 | BD (A = C/F/G/H)[c] |
| RDYVDRFYKTL | 8 | HLA-B44 | P24 | B/D (A = C/F/G/H)[c] |
| DRFYKTLRA | 9 | HLA-B14 | p24 | B/D (A = C/F/G/H) |
| AIFQSSMTK | 10 | HLA-A*0301, A11, A33 | pol | a/B/c/D/G/H |
| ITLWQRPLV | 11 | HLA-A*6802 | pol | a/b/C/D/F/G/H |
| ERYLKDQQL | 12 | HLA-B14 | gp41 | a/b/C/D |
| YLKDQQLL | 13 | HLA-A24, B8 | gp41 | a/b/C/D |
| TVYYGVPVWK | 14 | HLA-A*0301 | gp120 | A/B/C/D/g |
| RPQVPLRPMTY | 15 | HLA-B51 | nef | A/b/D/E/F/G |
| QVPLRPMTYK | 16 | HLA-A*0301, A11 | nef | A/b/D/E/F/G |
| VPLRPMTY | 17 | HLA-B35 | nef | A/b/D/E/F/G |
| AVDLSHFLK | 18 | HLA-A11 | nef | a/B/d/f |
| DLSHFLKEK | 19 | HLA-A*0301 | nef | A/B/D/F |
| FLKEKGGL | 20 | HLA-B8 | nef | A/B/C/D/E/F/G |
| ILKEPVHGV | 21 | HLA-A*0201 | pol | A/B/C/D/G |
| ILKEPVHGVY | 22 | HLA-Bw62 | pol | A/B/D |
| HPDIVIYQY | 23 | HLA-B35 | pol | a |
| VIYQYMDDL | 24 | HLA-A*0201 | pol | A/B/C/D/F/G/H |
| TPGPGVRYPL | 25 | HLA-B7 | nef | b/c |
| ACTPYDINQML[d] | 1 | Mamu-A*01 | p27 | SIV |
| RGPGRAFVTI[e] | 2 | H-2D[d] | env | HIV |

[a]Epitopes are listed (Seq. ID Nos. 3-25, 1, 2) in the order in which they appear in the polyepitope.
[b]A particular epitope sequence is present in about 50% (small letter) or 90% (capital letter) of sequenced HIV clade isolates.
[c]'=' indicates that the epitopes are present in the N-terminal clade A gag domain.
[d]A dominant epitope derived from SIV gag p27 flanked by Ala and Leu at its N- and C- termini, respectively, recognised by rhesus macaque CTL, which can be used for potency studies in rhesus macaques.
[e] A CTL epitope presented by a murine MHC class I used for the mouse potency assay.

Since it was intended to adopt a "prime/boost" protocol, in which priming was achieved by administering nucleic acid, it was desirable to design the sequence of the nucleic acid encoding the HIVA immunogen in order to increase the expression of HIVA in human cells. Firstly, to ensure an efficient initiation of translation from the first methionine codon, the HIVA open reading frame (ORF) was preceded by a 12-nucleotide-long Kozak consensus sequence (Kozak 1987 Nucl. Acids Res. 15, 8125-8148). Secondly, the translation of the resulting mRNA was optimised by substituting most of the HIV-1-derived codons with frequently used codons in highly expressed human genes (Andre et al, 1998, cited above). The HIVA ORF is a part of a 1,608-base pair-long double-stranded DNA HindIII-XbaI fragment. (FIG. 2A shows the nucleotide sequence of the HindIII-XbaI insert containing the HIVA ORF; Seq. ID No. 27) In FIG. 2A, the endonuclease sites used to assemble the partial PCR products are included (nucleotides 1-6=HindIII; 319-324=Bam HI; 712-717=KpnI; 1135-1140=EcoRI; and 1603-1608—XbaI).

Figure 2B:
FIG. 2B is a schematic representation of the method used to construct the HIVA gene.

Plasmid DNA was prepared and treated using standard protocols (Sambrook et al, "Molecular Cloning. A Laboratory Manual" $2^{nd}$ Edition; Cold Spring Harbor). The HIVA gene was constructed (as indicated in FIG. 2B) in vitro in four parts. Each part was prepared by assembly from overlapping positive- and negative-strand oligodeoxynucleotides of 70-90 bases in length. The synthetic oligodeoxynucleotides were purified using the EconoPure™ Kit (Perkin Elmer) according to the manufacturer's instructions, annealed and ligated, followed by PCR assembly. The PCR products were gel-purified after each step until fragments with the expected, unique terminal restriction endonuclease sites were obtained. These four products were cloned and sequenced, and ligated together to generate the complete HIVA gene. The HIVA gene was then inserted into the pTHr construct and MVA vaccine vector, as described below.

The pTHr Vector. A vector pTHr for a direct gene transfer was designed with the aim to minimise the number of functional elements and therefore the amount of DNA required to be administered.

Figure 3:
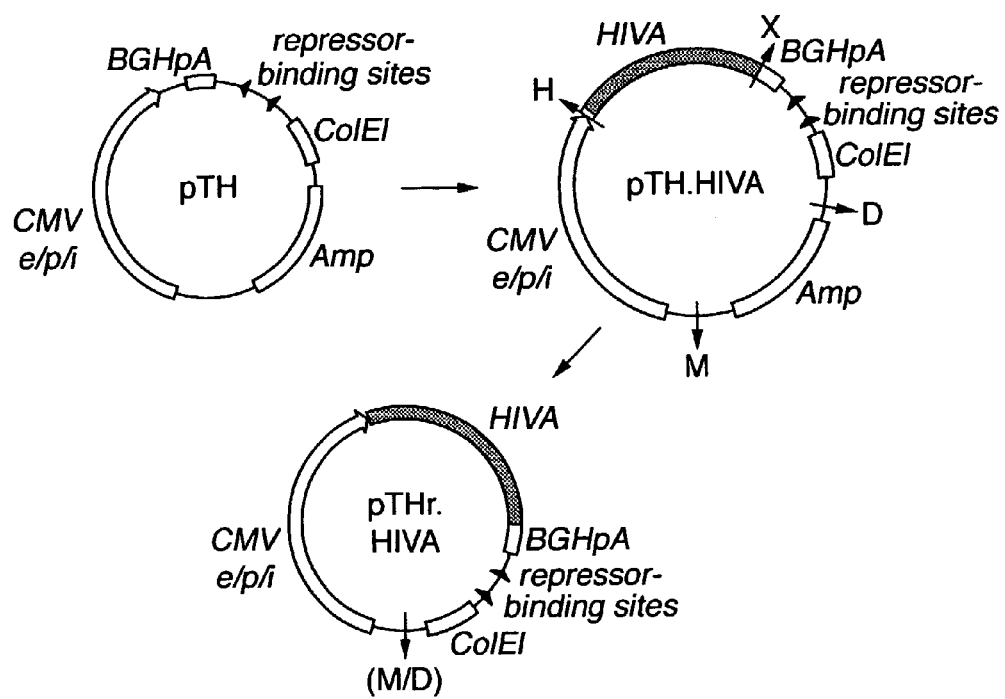
FIG. 3 is a schematic representation of a DNA vector molecule (pTHr. HIVA) in accordance with the invention, and the method of its construction.

The construction of pTH was described previously (Hanke et al, 1998 Vaccine 16, 426-435). It contains an expression efficient enhancer/promoter/intron A cassette of the human cytomegalovirus (hCMV) strain AD169 genome (Whittle et al, 1987 Protein Eng. 1, 499-505; Bebbington 1991 Methods 2, 136-145). The promoter region is followed by the pRc/CMV (Invitrogen)-derived polylinker and polyadenylation signal of the bovine growth hormone gene. The β-lactamase gene conferring ampicillin resistance to transformed bacteria and prokaryotic origin of double-stranded DNA replication ColE1 are both derived from plasmid pUC19. pTH does not contain an origin for replication in mammalian cells. After insertion of the HIVA DNA into the pTH polylinker, the β-lactamase gene fragment between the MluI and DraI sites was removed and the resulting construct pTHr.HIVA (FIG. 3) was propagated in bacteria using the repressor-titration system developed by Cobra Pharmaceuticals Ltd. (Keele, UK), which selects plasmid-carrying bacteria without the need for the presence of an antibiotic-resistance gene on the plasmid (Williams et al, 1998 Nucl. Acids Res. 26, 2120-2124). Therefore, DNA vaccination does not introduce into the human vaccinee large numbers of copies of an antibiotic resistance gene. Construction of pTHr. HIVA is illustrated schematically in FIG. 3 (CMV e/p/i=human CMV enhancer/promoter/intron A cassette; BGHpA=bovine growth hormone polyadenylation signal; ColE1=origin of dsDNA replication in bacteria; arrow head symbols denote repressor-binding sequences).

293T cells (and chicken embryo fibroblasts [CEF] were maintained in Dulbecco's modified Eagle's medium (DMEM; Gibco) supplemented with 10% foetal bovine serum (FBS; Gibco); 2 mM L-glutamine and penicillin/streptomycin. Cells were cultured in a humidified incubator in 5% $CO_2$ at 37° C. 293T cells were transiently transfected with pTHr. HIVA using the DEAE-dextran-chloroquine method (Hanke et al, 1998 Vaccine 16, 426-435). Briefly, $2.5 \times 10^5$ 293T cells were grown on coverslips in 6-well tissue culture plates overnight. The following day, cells were transfected with 5 g per well of DNA. After 48 hours, the transfected cells were fixed, their membranes were permeabilized and the SV5-P-k mAb followed by anti-murine FITC-conjugated antibodies were used to detect the expressed recombinant proteins.

Figure 4:
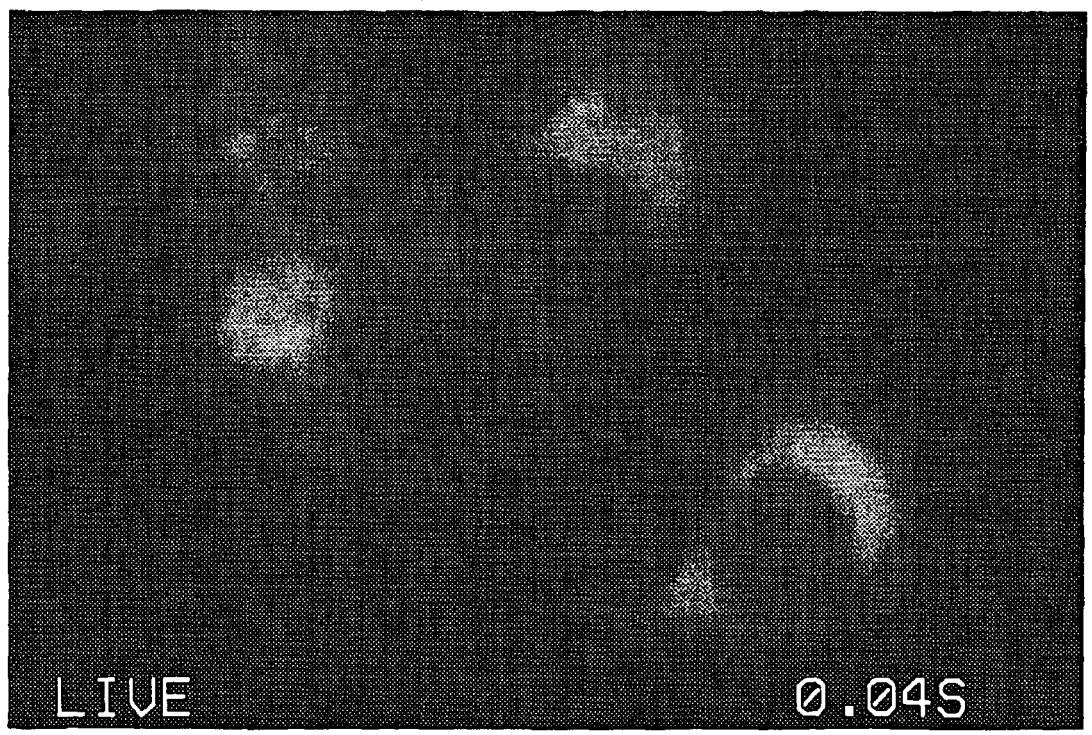
FIG. 4 is a micrograph showing immunofluorescent detection of HIVA expression by mouse cells following transfection with pTHr. HIVA.

A micrograph illustrating specimen results is shown in FIG. 4. The Figure shows three transfected cells and one background untransfected cell (top left).

Boosting was to be achieved by administering an MVA vector expressing the HIVA immunogen. MVA is an attenuated vaccinia virus safe for clinical application, which has almost lost its ability to replicate in human cells (Mayr et al, 1975 Infection 105, 6-14). The use of MVA as a vaccine vehicle and its features which make it an attractive choice among the attenuated poxvirus vectors (see, e.g. Sutter et al, 1994 Vaccine 12, 1032-1040; and Moss et al, 1996 Adv. Exp. Med. Biol. 397, 7-13) have been described extensively.

The HIVA gene was ligated into plasmid pSC11, which directed the gene into the thymidine kinase locus of the parental MVA (Carroll & Moss 1995 Biotechniques 19, 352-356). Bulk stocks of the recombinant MVA were grown on primary CEF obtained from the eggs of a specific pathogen-free flock. MVA was purified by centrifugation of cytoplasmic extracts through a 36% (w/v) sucrose cushion in a Beckman SW28 rotor at 13,500 rpm for 80 minutes. Taking advantage of the co-inserted β-galactosidase gene, the virus stock titres were determined from the number of blue plaques after incubation of the infected cell monolayers with the appropriate substrate.

Vaccine Potency Assay. The potencies of the DNA and MVA vectors were tested in groups of Balb/c mice taking advantage of the presence of the $H-2D^d$-restricted epitope (Takahashi et al, 1993 Int. Immunol. 5, 849-857). For the pTHr.HIVA DNA vaccine, mice were either needle-injected intramuscularly with 100 μg of DNA or immunised twice 3 weeks apart intradermally with total of 2 μg of DNA using the Dermal XR gene delivery device of PowderJect Vaccines Inc. (Madison, Wis., U.S.A.). The mice were sacrificed 10 or 21 days after the last immunisation. Spleens from the immunized mice were removed and pressed individually through a cell strainer (Falcon) using a 2-ml syringe rubber plunger. The splenocytes were washed and divided into two halves. One half was frozen for tetramer analysis and the second half was suspended in 5 ml of Lymphocyte medium (R10, 20 mM HEPES and 15 mM β-mercaptoethanol) and restimulated in vitro by incubation with 2 μg/ml of the RGPGRAFVTI (Seq. ID No. 2) peptide in an humidified incubator in 5% $CO_2$ at 37° C. for 5 days.

The effector cells were 2-fold diluted in U-bottom wells (96-well plate; Costar) starting with 100:1 effector to target ratio. Five thousand $^{51}$Cr-labeled P815 target cells in a medium without or supplemented with $10^{-6}$ M peptide was then added to the effectors and incubated at 37° C. for 5 hours. Spontaneous and total chromium releases were estimated from wells, in which the target cells were kept in a medium alone or with 5% Triton X-100, respectively. The percentage specific lysis was calculated as [(sample release−spontaneous release)/(total release−spontaneous release)]×100. The spontaneous release was lower than 5% of the total c.p.m.

Figure 5B:
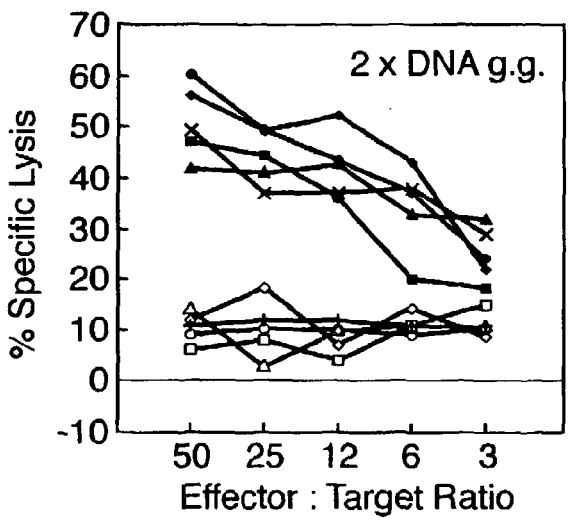
Figure 5C:
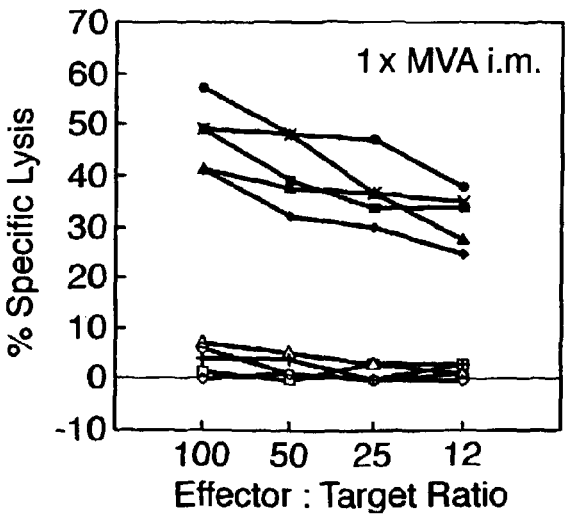

The results of typical assays are shown in FIGS. 5A-C, which are graphs of % specific lysis against Effector: Target ratio. FIG. 5A shows results for splenocytes obtained from mice immunised once with 100 μg of pTHr.HIVA DNA. FIG. 5B shows results from mice immunised twice intradermally with pTHr. HIVA DNA. FIG. 5C shows results obtained from mice immunised intramuscularly with 10⁷ pfu of MVA-.HIVA. In each of FIGS. 5A-5C, each line represents a single mouse. Lysis of peptide-pulsed targets is denoted by filled symbols, unpulsed targets by open symbols.

Both modes of the pTHr.HIVA vector delivery were highly immunogenic and induced high cytolytic activities in all immunised animals (see FIGS. 5A & B). Similarly, a single needle intramuscular injection of 10⁷ plaque-forming units of MVA.HIVA elicited in all vaccinees strong peptide-specific lytic activities measured after a culture restimulation (FIG. 5C).

Example 2

Further nucleic acid constructs were prepared which encoded polyprotein immunogens based on HIVA, but comprising further HIV antigen components. These further constructs and their encoded immunogens were termed HIVTA and HIVAeT, as shown in FIG. 1A. Also shown is a construct/immunogen termed PPA. The relevant DNA/amino acid sequences are shown in FIGS. 6 A/B-8 A/B respectively, although FIG. 7A shows only that portion of amino acid sequence in HIVA eT (attributable to tat) which is additional to that in HIVTA. (Note that the sequence of the HindIII and XbaI sites at the 5' and 3' ends of the DNA sequences are not shown in FIGS. 6B, 7B and 8B). The constructs were prepared in a manner similar to that described above for HIVA.

HIVTA and HIVAeT share the same design rationale with HIVA, but additionally include the HIV-1 clade A tat sequence, expressed either as part of a fusion protein with gag and the polyepitopic synthetic polypeptide (in the case of HIVTA, the tat sequence being positioned between gag and the synthetic polypeptide), or else being present on the same construct but expressed as a separate polypeptide (in the case of HIVAeT), by virtue of the inclusion of an internal ribosome entry site (IRES).

Each of the nucleic acid molecules may be used to immunise subjects, in a manner similar to that described above in relation to HIVA DNA. Equally, the molecules may be introduced into appropriate vectors, especially MVA, again as described above in Example 1, and the resulting vector used to immunise subjects.

The significance of the genetic diversity among individual HIV isolates and its implication for vaccine design have been long debated. The predominant HIV-1 clade in Europe and North America is clade B, which is also the most studied one. In central and Eastern Africa, the predominant circulating HIV-1 strain is clade A, while lade C is dominating Southern Africa, India and China. Generally, a clade-specific vaccine design requires a more careful consideration for the induction of nAb than for CTL. Although there are some important inter-clade differences in CTL epitopes, many epitopes are conserved across clades partially due to structure/function constraints. However, to facilitate the interpretation of efficacy studies, vaccines should attempt to match the local strains prevalent in the trial population with the view that any successful approaches can be adapted for other clades if cross-protection is not achieved.

The invention claimed is:

1. An immunogen comprising the amino acid sequence shown in FIG. 1B.

2. A polypeptide comprising the amino acid sequence shown in FIG. 8A.

3. An immunogen in sterile form suitable for administration to a human subject, the immunogen comprising one of the following structures:
   (a) NH2-p24-p17-CTL polyepitope-COOH;
   (b) NH2-p24-p17-tat-CTL polyepitope-COOH;
   (c) NH2-p24-p17-CTL polyepitope-tat-COOH; or
   (d) NH2-p24-p17-C pol-rev-tat-nef-N pol-CTL polyepitope-COOH;
   wherein the CTL polyepitope comprises at least 10 of the human CTL epitopes identified in Table 1.

4. An immunogen according to claim 3, in which p17 is modified to prevent N-terminal myristylation.

5. An immunogen according to claim 3, in which at least some of the human CTL epitopes present in the synthetic polypeptide are overlapping.

6. An immunogen according to claim 3, in which at least 50% of the human CTL epitopes present in the synthetic polypeptide are overlapping.

7. An immunogen according to claim 3, in which at least some of the human CTL epitopes present in the synthetic polypeptide are adjacent.

8. An immunogen in according to claim 3, in which at least some of the human CTL epitopes are separated by non-epitopic amino acid sequences.

9. An immunogen according to claim 3, comprising at least one epitope which is recognized by one or more laboratory test mammals.

10. An immunogen according to claim 9, wherein said epitope recognized by one or more laboratory test mammals is a CTL epitope.

11. An immunogen according to claim 3, in which the synthetic polypeptide comprises at least 15 of the human CTL epitopes identified in Table 1.

12. An immunogen according to claim 3, in which the synthetic polypeptide comprises at least 20 of the human CTL epitopes identified in Table 1.

13. An immunogen according to claim 3, in which the synthetic polypeptide comprises at least 23 of the human CTL epitopes identified in Table 1.

14. A bacterium comprising an immunogen in accordance with claim 3.

15. The bacterium according to claim 14 which is an attenuated pathogen suitable for administration to a human subject.

* * * * *